United States Patent
Boudreaux

(10) Patent No.: US 10,166,065 B2
(45) Date of Patent: Jan. 1, 2019

(54) DEVICES AND METHODS FOR CLAMPING AND CUTTING TISSUE

(71) Applicant: Ethicon Endo-Surgery, Inc., Cincinnati, OH (US)

(72) Inventor: Chad P. Boudreaux, Cincinnati, OH (US)

(73) Assignee: Ethicon LLC, Guaynabo, PR (US)

(*) Notice: Subject to any disclaimer, the term of this patent is extended or adjusted under 35 U.S.C. 154(b) by 819 days.

(21) Appl. No.: 14/558,836

(22) Filed: Dec. 3, 2014

(65) Prior Publication Data
US 2016/0157926 A1    Jun. 9, 2016

(51) Int. Cl.
| | |
|---|---|
| *A61B 18/00* | (2006.01) |
| *A61B 18/14* | (2006.01) |
| *A61B 17/295* | (2006.01) |
| *A61B 17/00* | (2006.01) |
| *A61B 17/29* | (2006.01) |

(52) U.S. Cl.
CPC ........ *A61B 18/1445* (2013.01); *A61B 17/295* (2013.01); *A61B 17/2909* (2013.01); *A61B 18/1447* (2013.01); *A61B 2017/00367* (2013.01); *A61B 2017/294* (2013.01); *A61B 2017/2916* (2013.01); *A61B 2017/2936* (2013.01); *A61B 2018/0063* (2013.01); *A61B 2018/1455* (2013.01)

(58) Field of Classification Search
CPC .................. A61B 18/1445; A61B 17/2909
USPC ........................................................ 606/51
See application file for complete search history.

(56) References Cited

U.S. PATENT DOCUMENTS

| | | |
|---|---|---|
| 5,624,452 A | 4/1997 | Yates |
| 2006/0151567 A1 | 7/2006 | Roy |

(Continued)

FOREIGN PATENT DOCUMENTS

| | | |
|---|---|---|
| EP | 0694291 A1 | 1/1996 |
| EP | 2486860 A2 | 8/2012 |

OTHER PUBLICATIONS

Ethicon Endo-Surgery ECHELON FLEX™ ENDOPATH® Stapler: Steps-to-use. 2011.

(Continued)

*Primary Examiner* — Nadia A Mahmood
(74) *Attorney, Agent, or Firm* — Mintz Levin Cohn Ferris Glovsky and Popeo, P.C.

(57) ABSTRACT

Various exemplary devices and methods are provided for clamping and cutting tissue. In general, a surgical device is provided having a handle and an elongate shaft extending distally therefrom with opposed jaws coupled to the elongate shaft's distal end. First and second movable handles of the device's handle can be configured to move together during a first phase of travel, and the second movable handle can be configured to move relative to the first movable handle during a second phase of travel. In the first phase of travel, the first movable handle's movement can cause the jaws to move from an open position to a closed position. In the second phase of travel, the second movable handle's movement can cause a cutting element to translate through the jaws. The second phase of travel can be prevented from occurring until the first phase of travel has been completed.

13 Claims, 19 Drawing Sheets

(56) References Cited

U.S. PATENT DOCUMENTS

| | | | |
|---|---|---|---|
| 2007/0118163 A1* | 5/2007 | Boudreaux | A61B 17/064 606/157 |
| 2008/0132893 A1 | 6/2008 | D'Amelio et al. | |
| 2008/0210738 A1* | 9/2008 | Shelton | A61B 17/064 227/176.1 |
| 2012/0022529 A1 | 1/2012 | Shelton, IV et al. | |
| 2012/0074201 A1 | 3/2012 | Baxter, III et al. | |
| 2012/0078139 A1 | 3/2012 | Aldridge et al. | |
| 2012/0116379 A1 | 5/2012 | Yates et al. | |
| 2012/0172873 A1 | 7/2012 | Artale et al. | |

OTHER PUBLICATIONS

LigaSure™: Blunt Tip Laparoscopic Sealer/Divider. Instructions for Use. Aug. 2009.
U.S. Appl. No. 14/166,194, filed Jan. 28, 2014.
International Search Report and Written Opinion for Application No. PCT/US2014/069492 dated Apr. 30, 2015.
International Preliminary Report on Patentability for Application No. PCT/US2015/063712 dated Jun. 6, 2017.

\* cited by examiner

DEVICES AND METHODS FOR CLAMPING AND CUTTING TISSUE

FIELD OF THE INVENTION

The present disclosure relates generally to devices and methods for clamping and cutting tissue.

BACKGROUND

In recent years surgery has markedly advanced through the performance of laparoscopic and endoscopic surgical procedures such as cholecystectomies, gastrostomies, appendectomies, and hernia repair. Laparoscopic surgery, which can also be referred to as minimally invasive surgery, is a surgical technique that includes operations performed through small incisions in the body of a patient. There can be a number of advantages to the patient with laparoscopic surgery compared to open procedures where larger incisions are made. For example, pain and hemorrhaging can be reduced due to the smaller incisions and recovery times can be shorter.

In a conventional laparoscopic procedure, a distal end of a laparoscopic or electrosurgical device can be passed through a small incision in the skin of a patient. The distal end of the laparoscopic device is then positioned at or adjacent a surgical site. One or more surgical procedures are then performed at the surgical site, which can include cutting and/or sealing tissue. The distal end of the laparoscopic device can be removed from the patient after the completion of the surgical procedure.

Many laparoscopic devices include a pair of jaws for grasping or otherwise effecting tissue. Movement of the jaws between open and closed positions is controlled by an actuation assembly, which transmits a force from the handle to the opposed jaws. The force required to close the jaws can increase with thicker or stiffer tissue, and/or in applications where the jaws are applying a closure mechanism, such as a clip or staple, to the tissue. The actuation assembly can require manual application of force by a user to actuate the actuation assembly, and this manual force can become difficult to apply when the force required to actuate the actuation assembly becomes great, such as in the case of thicker or stiffer tissue. In the event that excessive forces are transmitted by the actuation assembly, undesired damage to the tissue can result. In addition, since the actuation assembly requires precise timing and coordinated movement between numerous components, excessive forces applied to close the jaws can result in damage to the components of the actuation assembly.

Accordingly, there remains a need for improved devices and methods for clamping and cutting tissue.

SUMMARY

A surgical device is provided that in one embodiment includes a proximal handle portion with a stationary handle, a first movable handle, and a second movable handle. The second movable handle can be locked to the first movable handle during a first phase of travel from a first initial position to a second, intermediate position such that the first and second movable handles move together as a unit toward the stationary handle during the first phase of travel. The second movable handle can be unlocked from the first movable handle during a second phase of travel from the second position to a third and final position. The device can also include an elongate shaft extending distally from the handle portion, first and second jaws at a distal end of the elongate shaft, and a cutting element configured to move through the first and second jaws so as to cut tissue engaged by the first and second jaws in response to the second movable handle moving toward the stationary handle during the second phase of travel. The first and second jaws can be configured for relative movement between an open position and a closed position, and the first and second jaws can be configured to move from the open position to the closed position during the first phase of travel.

The device can have any number of variations. For example, the first movable handle in the second position can be locked in position relative to the stationary handle of the surgical device, and the first movable handle can remain in the locked position during the second phase of travel. For another example, the device can include one or more electrodes coupled to at least one of the first and second jaws. The one or more electrodes can be configured to apply radiofrequency (RF) energy to the tissue engaged by the first and second jaws. For yet another example, the device can include a spring disposed within the proximal handle portion. The spring can be configured to apply a bias force to the second movable handle to hold the second movable handle in a fixed position after the first phase of travel. The movement of the second movable handle during the second phase of travel can be configured to overcome the bias force. For still another example, during at least the first phase of travel at least one of the first and second jaws can be configured to apply RF energy to tissue clamped between the first and second jaws.

In some embodiments, the device can include a cam slot formed in the second movable handle. The slot can include a pin locking cut out and a pin travel portion. The device can also include a pin configured to move within the cam slot between the pin locking cut-out and the pin travel portion of the slot. The pin can be configured to be seated in the locking cut-out when the first and second movable handles are moving together, and the pin can be configured to slide in the pin travel portion of the slot during the second phase of travel. In some embodiments, the device can include a cam lever within the proximal handle portion. The cam lever can have a second slot formed therein that includes a first leg and a second leg that extends transverse to the first leg, and the cam lever can include a second pin configured to move between the first leg and the second leg. The second pin can be configured to slide in the first leg during the first phase of travel, and the second pin can be configured to slide in the second leg during the second phase of travel. In some embodiments, the cam lever can be configured to push the pin through the elongate portion of the slot.

In some embodiments, the device can include a pin seated in a first slot formed in the first movable handle and seated in a second slot formed in the second movable handle. The second slot can be offset at an angle from the first slot. The proximal handle portion can include a housing that has a third slot formed therein. The third slot can be configured to force the pin into a first position in which the second movable handle is locked to the first movable handle during the first phase of travel, and to force the pin into a second position in which the second movable handle is unlocked from the first movable handle during the second phase of travel.

In another embodiment, a surgical device is provided that includes a proximal handle portion, an elongate shaft extending distally from the proximal handle portion, an end effector coupled to a distal end of the elongate shaft, and a cutting element. The proximal handle portion can include a body portion having a first slot formed therein, a first trigger configured to move relative to the body portion in a first actuation of the proximal handle portion, a second trigger having a second slot formed therein that has an elongate portion and a cut-out region adjacent to and in communication with the elongate portion, and a first pin operatively coupled to and movable within the second slot. The second trigger can be configured to move relative to the body portion simultaneously with the first trigger in the first actuation, and the second trigger can be configured to move relative to the first trigger and the body portion in a second actuation of the proximal handle portion. The first pin can be configured to remain within the second slot during the first actuation, and the first pin can be configured to slide in the elongate portion of the second slot during the second actuation. The end effector can be configured to move from an open position to a closed position in response to the first actuation. The cutting element can be configured to translate through the end effector in response to the second actuation.

The device can vary in any number of ways. For example, in response to the first actuation, the first pin can be configured to automatically move to the elongate portion of the second slot from the cut-out region of the second slot. For another example, the device can include a spring configured to move into contact with a surface of the second trigger in response to the first actuation so as begin applying a force to the second trigger. In some embodiments, the spring can be configured to slide along the surface of the second trigger during the second actuation. In some embodiments, the force applied by the spring can be configured to fix the second trigger in position with respect to the body portion and the first trigger until a manual force applied to the second trigger overcomes the force applied by the spring.

In another aspect, a surgical method is provided that in one embodiment includes actuating a first trigger of a surgical device to simultaneously move the first trigger and a second trigger from a first position to a second position, thereby causing a spring to contact the second trigger and begin applying a force to the second trigger. Movement of the first and second triggers can cause first and second jaws of the surgical device to clamp tissue therebetween. The method can also include moving the second trigger, relative to the first trigger, from the second position to a third position, thereby reducing the force applied by the spring to the second trigger, and thereby causing passage of the knife blade along one of the first and second jaws to cause the clamped tissue to be cut.

The method can have any number of variations. For example, moving the second trigger relative to the first trigger can cause the spring to translate along a surface of the second trigger. For another example, the method can include moving the second trigger from the third position to the second position and then simultaneously moving the first and second triggers from the second position to the first position. The spring can cause the second trigger to move simultaneously with the first trigger from the second position to the first position. For yet another example, moving the second trigger from the second position to the third position can cause RF energy to be applied to the clamped tissue. For still another example, simultaneously moving the first and second triggers can include applying a manual force to the second trigger.

In some embodiments, a first pin seated in a first slot formed in the second trigger can remain stationary in the first slot during the simultaneous movement of the first and second triggers so as to prevent movement of the first trigger relative to the second trigger, and the first pin can move within the first slot during movement of the second trigger relative to the first trigger. In some embodiments, the simultaneous movement of the first and second triggers can cause a second pin seated in a first leg of a second slot formed in a cam member of the surgical device to move within the first leg, and the movement of the second trigger relative to the first trigger can cause the second pin to move within a second leg of the second slot that is transverse to the first leg and can cause the cam member to move the first pin within the first slot.

BRIEF DESCRIPTION OF THE DRAWINGS

This invention will be more fully understood from the following detailed description taken in conjunction with the accompanying drawings, in which.

DETAILED DESCRIPTION

Figure 1:
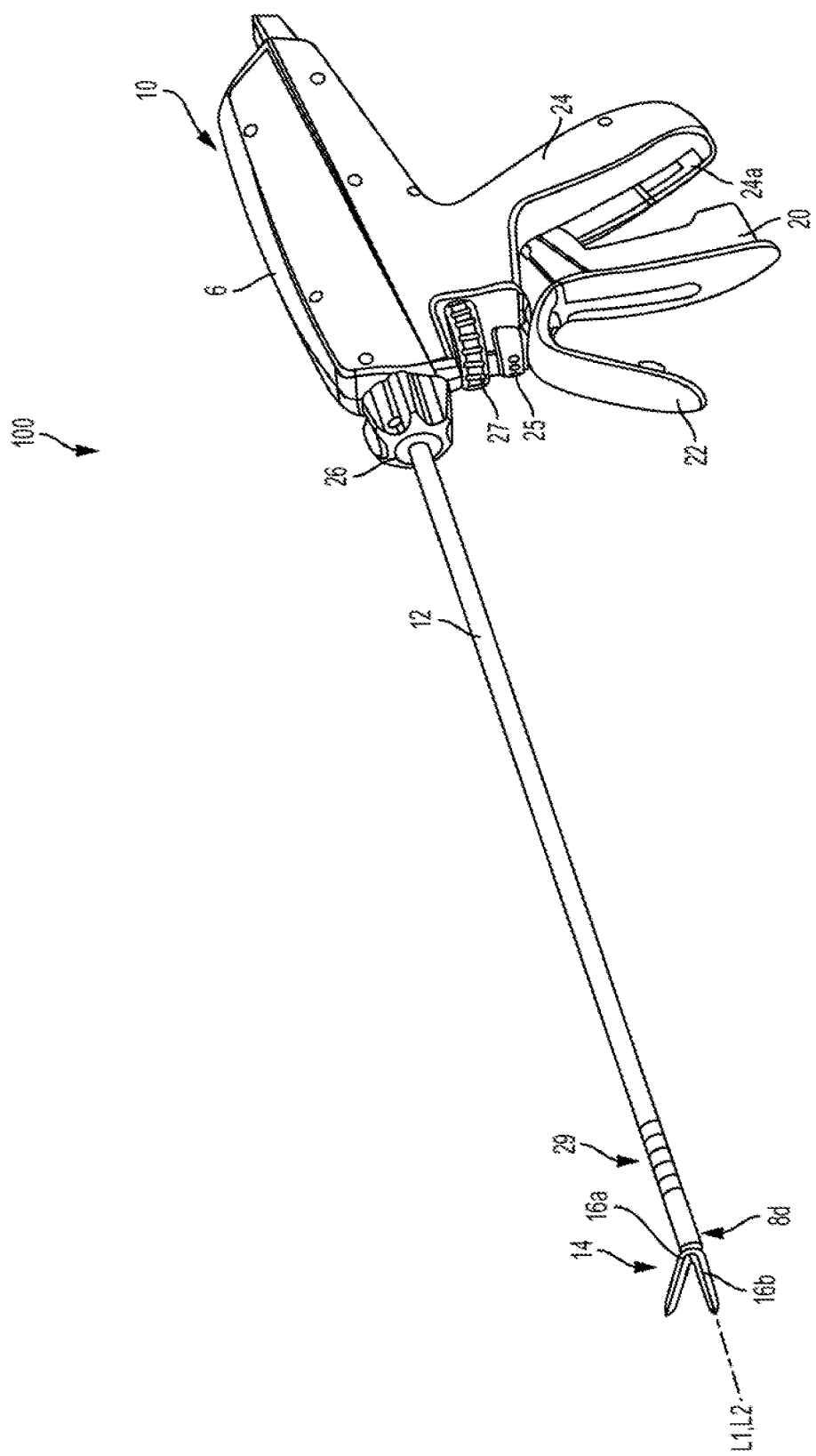
FIG. 1 is a perspective schematic view of one embodiment of a surgical device configured to clamp and cut tissue.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary devices and methods are provided for clamping and cutting tissue. In general, a surgical device is provided having a handle and an elongate shaft extending distally therefrom with opposed jaws coupled to a distal end of the elongate shaft. The handle can include first and second movable handles. The first movable handle can be configured to move between an open position and a closed position for causing corresponding movement of the jaws between open and closed positions. The second movable handle can be configured move between an open position and a closed position for causing a cutting element to translate through the jaws and cut tissue clamped between the jaws, e.g., when the jaws are in the closed position. The first and second movable handles can be configured to move together during a first phase of travel, and the second movable handle can be configured to move relative to the first movable handle during a second phase of travel. In the first phase of travel, the first movable handle's movement can cause the jaws to move from the open position to the closed position. The movement of the second movable handle during the first phase of travel can have no effect on the cutting element, e.g., the cutting element can remain in a stationary position relative to the jaws during the first phase of travel. Tissue can thus be clamped between the jaws in the closed position. In the second phase of travel, the second movable handle's movement can cause the cutting element to translate through the jaws, thereby cutting the tissue clamped between the jaws during the first phase of travel. The second phase of travel can be prevented from occurring until the first phase of travel has been completed, e.g., until the first movable handle has moved through its full phase of movement, which can help improve safety and/or help increase user control over clamping and cutting. In other words, the device can be configured to prevent the cutting of tissue until the jaws have been closed.

The first and second movable handles can be arranged such that a single hand of a user can engage both of the first and second movable handles in a single stroke including both the first and second phases of travel. The user can thus cause jaw closure and tissue cutting in one stroke without requiring repositioning of the user's hand between closure and cutting. The arrangement of the first and second movable handles to allow for single hand actuation of the first and second movable handles can provide for a low grip span such that hands of many different sizes can engage and move the first and second movable handles.

The surgical device can include a bias element configured to cooperate with the second movable handle in the second phase of travel. The bias element can be configured to only be in contact with the second movable handle during the second phase of travel so as to not apply a force to the second movable handle until the first phase of travel has been completed. The force applied by the bias element to the second movable handle thus need not be overcome during the first phase of travel since the force has not yet been applied, which can make it easier to close the jaws and/or can reduce chances of excess force being applied to the device so as to cause any damage thereto during the first phase of travel. The force applied by the bias element to the second movable handle can be configured to gradually decrease during the second phase of travel, which can help allow a lower force to be applied by a user to the second movable handle to effect the cutting of tissue. Particularly with tissue that is difficult to cut, such as if the tissue is thick, tough, irradiated, and/or calcified, this reduced amount of user-applied force can provide for a better user experience, smoother cutting of the clamped tissue, and/or reduced chances of excess force being applied to the device so as to cause any damage thereto.

The surgical device can be configured to seal tissue positioned between the opposed jaws, such as by applying energy, e.g., RF energy, to the tissue. The movement of the second movable handle in the second phase of travel can cause the energy can be applied. In some embodiments, the movement of the second movable handle in the second phase of travel can only cause the cutting element to cut the clamped tissue, e.g., cut without sealing. Causing cutting without also causing sealing can help reduce a number of parts of the device, which can make the device easier to manufacture and/or can reduce a cost of the device. In some embodiments, the movement of the second movable handle in the second phase of travel can cause the cutting element to cut the clamped tissue and can cause the sealing of the clamped tissue. Causing both cutting and sealing can facilitate the quickest healing of tissue. The energy can be applied in a variety of ways, as will be appreciated by a person skilled in the art. Exemplary embodiments of sealing tissue by applying energy thereto are described in US Pat. Pub. No. 2012/0078139 entitled "Surgical Generator For Ultrasonic And Electrosurgical Devices" filed Oct. 3, 2011, US Pat. Pub. No. 2012/0116379 entitled "Motor Driven Electrosurgical Device With Mechanical And Electrical Feedback" filed Jun. 2, 2011, and U.S. application Ser. No. 14/166,194 entitled "Surgical Devices Having Controlled Tissue Cutting And Sealing" filed Jan. 28, 2014, which are hereby incorporated by reference in their entireties.

Figure 2:
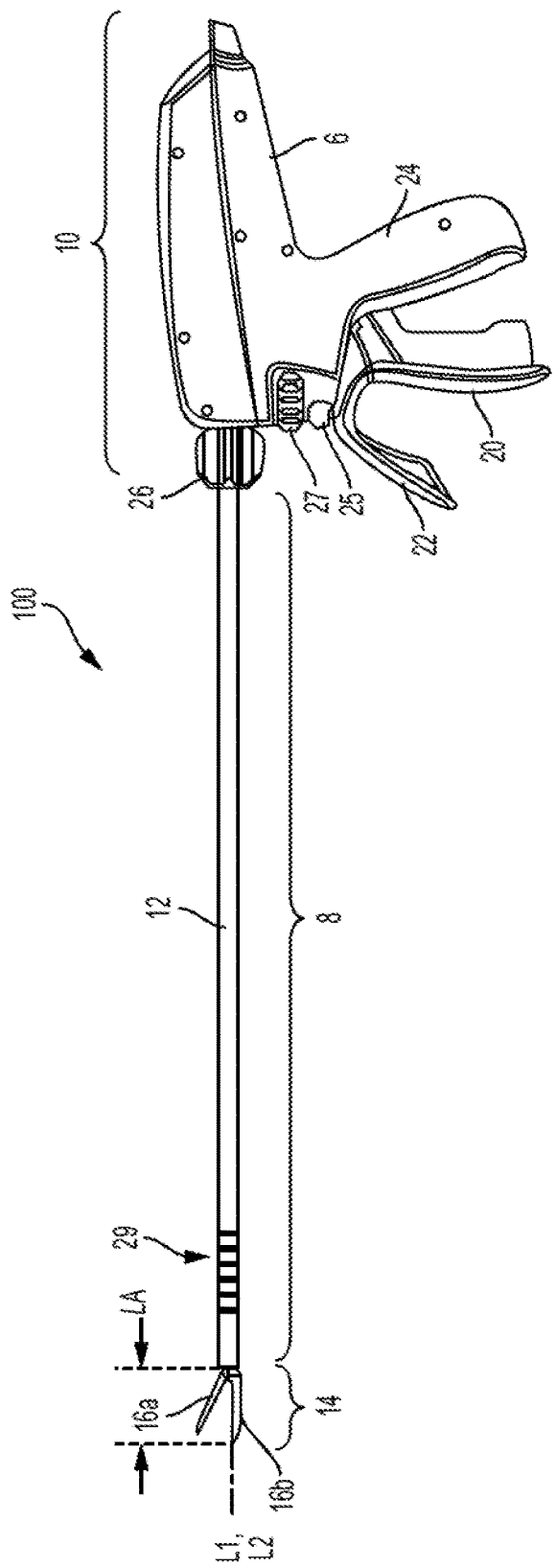
FIG. 2 is a side schematic view of the surgical device of FIG. 1.

FIGS. 1 and 2 illustrate one embodiment of a surgical device 100 configured to clamp and cut tissue. The device 100 can include a proximal handle portion 10, a shaft portion 8, and an end effector 14 coupled to a distal end of the shaft portion 8. The proximal handle portion 10 can be configured to have at least a portion thereof held by hand. The proximal handle portion 10 can be configured to carry various actuators configured to actuate the end effector 14, as discussed further below. As in the illustrated embodiment, the proximal handle portion 10 can include a body portion 6 (also referred to as a "housing"), a first movable handle 20, a second movable handle 22, and a stationary handle 24. The "movable handles" are also referred to herein as "triggers." In general, the body portion 6 can be configured to house various elements therein that are configured to facilitate clamping and cutting of tissue, as discussed further below. The stationary handle 24 can form a portion of the housing 6 as in this illustrated embodiment. Movement of the first movable handle 20 toward and away from the stationary handle 24, such as by manual movement by a hand of a user, can adjust a position of the end effector 14. Movement of the second movable handle 22 toward and away from the stationary handle 24, such as by manual movement by a hand of a user, can cause tissue engaged by the end effector 14 to be cut, and in some embodiments, also have energy applied thereto. As discussed further below, the first and second movable handles 20, 22 can be configured to move in unison relative to the stationary handle 24 during a first phase of travel, and the second movable handle 22 can be configured to move relative to the first movable handle 20 and the stationary handle 24 during a second phase of travel. The shaft portion 8 can extend distally from the proximal handle portion 10 and can have a lumen 13 (shown in FIG. 4) extending therethrough. The bore can carry mechanisms for actuating the end effector 14, such as a jaw closure tube and/or a drive shaft.

The shaft portion 8 can have a variety of sizes, shapes, and configurations. The shaft portion 8 can include an elongate shaft 12, e.g., an outer shaft of the shaft portion 8. The device 100 can include a rotation mechanism configured to rotate the shaft portion 8 about a longitudinal axis L2 thereof. As in this illustrated embodiment, the rotation mechanism can include a knob 26, which can be configured to rotate to rotate the shaft portion 8. As in this illustrated embodiment, such rotation may provide rotation of the end effector 14 and the shaft portion 8 unitarily. In other embodiments, the rotation mechanism can be operable to rotate the end effector 14 without rotating any portion of the shaft portion 8 that is proximal of an articulation section 29 in a distal portion of the shaft portion 8. In other embodiments, the device 100 can include one rotation mechanism that provides rotatability of the shaft portion 8 and the end effector 14 as a single unit, and another rotation mechanism that provides rotatability of the end effector 14 without rotating any portion of the shaft portion 8 that is proximal of the articulation section 29. Other suitable rotation schemes will be apparent to those skilled in the art. In some embodiments, rotatable features may be omitted.

As in this illustrated embodiment, the device 100 can include an articulation mechanism configured to selectively control articulation of the end effector 14 about the articulation section 29. The articulation mechanism can have a variety of configurations, such as a knob 27 configured to rotate to effect the articulation, as in this illustrated embodiment. Actuation of the articulation mechanism, e.g., rotation of the knob 27, can be configured to cause articulation of the articulation section 29, thereby adjusting an angular orientation of the end effector 14. The articulation section 29 can have a variety of sizes, shapes, and configurations. As in this illustrated embodiment, the articulation section 29 can include a plurality of articulatable segments 31. The device 100 in this illustrated embodiment includes five segments 31, but it can include any number of segments 31. The articulation section 29 can be in a distal portion of the shaft portion 8 that is proximal to a distal-most end of the shaft portion 8 such that articulation of the articulation section 29 can articulate the end effector 14 as well as a distal-most portion of the shaft portion 8.

The end effector 14 can have a variety of sizes, shapes, and configurations. As shown in FIGS. 1-4, the end effector 14 can include a first, upper jaw 16a and a second, lower jaw 16b each disposed at a distal end 8d of the shaft portion 8. One or both of the upper and lower jaws 16a, 16b can be configured to close or approximate about a longitudinal axis L1 of the end effector 14. Both of the jaws 16a, 16b can be moveable relative to the shaft portion 8 such that the end effector 14 can be moved between open and closed positions, or only one the upper and lower jaws 16a, 16b can be configured to move relative to the elongate shaft 12 and to the other of the jaws 16a, 16b so as to move the end effector 14 between open and closed positions. In this illustrated embodiment, the upper jaw 16a is configured to move relative to the bottom jaw 16b, which is configured to remain stationary relative to the elongate shaft 12. When the end effector 14 is in the open position, as shown in FIGS. 1-4, the jaws 16a, 16b can be positioned at a distance apart from one another with space therebetween. As discussed further below, tissue can be positioned within the space between the jaws 16a, 16b. When the end effector 14 is in the closed position, a longitudinal axis of the upper jaw 16a can be substantially parallel to a longitudinal axis of the lower jaw 16b, and the jaws 16a, 16b can be moved toward one another such that the distance therebetween is less than when the end effector 14 is in the open position. In some embodiments, facing engagement surfaces 18a, 18b of the jaws 16a, 16b can be in direct contact with one another when the end effector 14 is in the closed position such that the distance between is substantially zero. In this illustrated embodiment, the upper jaw 16a is configured to pivot relative to the elongate shaft 12 and relative to the lower jaw 16b while the lower jaw 16b remains stationary. In this illustrated embodiment, the jaws 16a, 16b are curved along the longitudinal axis L1 of the end effector 14, but a person skilled in the art will appreciate that one or both of the jaws 16a, 16b can have a substantially elongate and straight shape. The longitudinal axis L1 of the end effector 14 can be parallel to and coaxial with a longitudinal axis of the elongate shaft 12 at least when the end effector 14 is in the closed configuration, and if the end effector 14 is configured to articulate relative to the elongate shaft 12, when the end effector 14 is not articulated relative to the elongate shaft 12.

Figure 3:
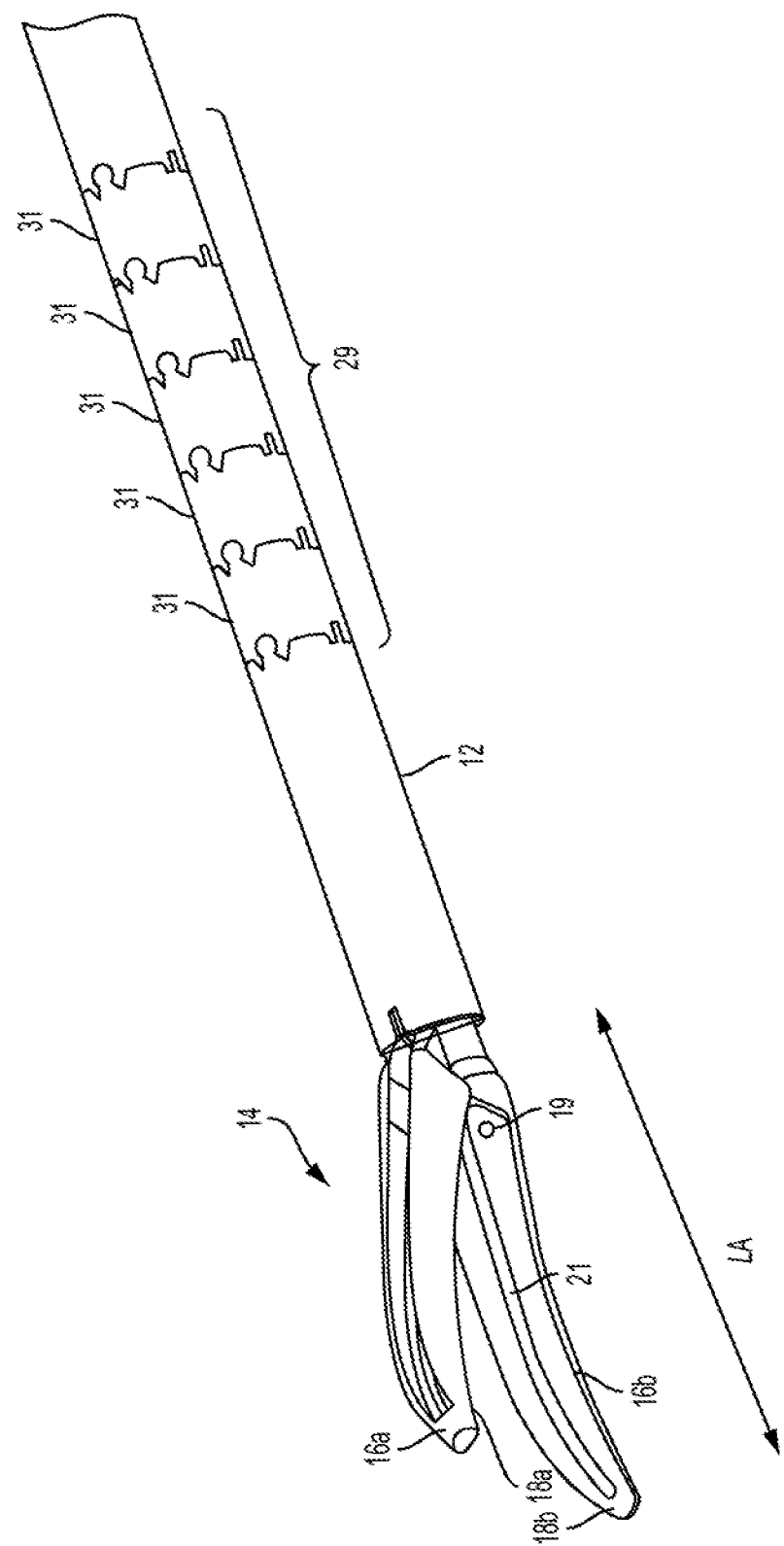
FIG. 3 is a perspective schematic view of a distal portion of the surgical device of FIG. 1.

The jaws 16a, 16b can have any suitable axial length LA for engaging tissue, where the axial length LA is measured along the longitudinal axis L1 of the end effector 14, as shown in FIGS. 2 and 3. The axial length LA of the jaws 16a, 16b can also be selected based on the targeted anatomical structure for transection and/or sealing. In an exemplary embodiment, the jaws 16a, 16b have a substantially equal axial length LA.

The jaws 16a, 16b can have any number and any combination of features configured to facilitate grasping tissue between the facing surfaces 18a, 18b of the jaws 16a, 16b. The first and second engagement surfaces 18a, 18b can each be configured to directly contact tissue. Either one or both of the engagement surfaces 18a, 18b can include one or more surface features (not shown) formed thereon that can help secure the tissue thereon. The one or more surface features can facilitate grasping of tissue, can be configured to increase friction between the tissue and the engagement surfaces 18a, 18b of the jaws 16a, 16b without tearing or otherwise damaging the tissue in contact with such surface features, and/or can facilitate forming substantially smooth, uniform layers of tissue to improve tissue effect. Examples of the surface features can include teeth, ridges, and depressions.

Figure 4:
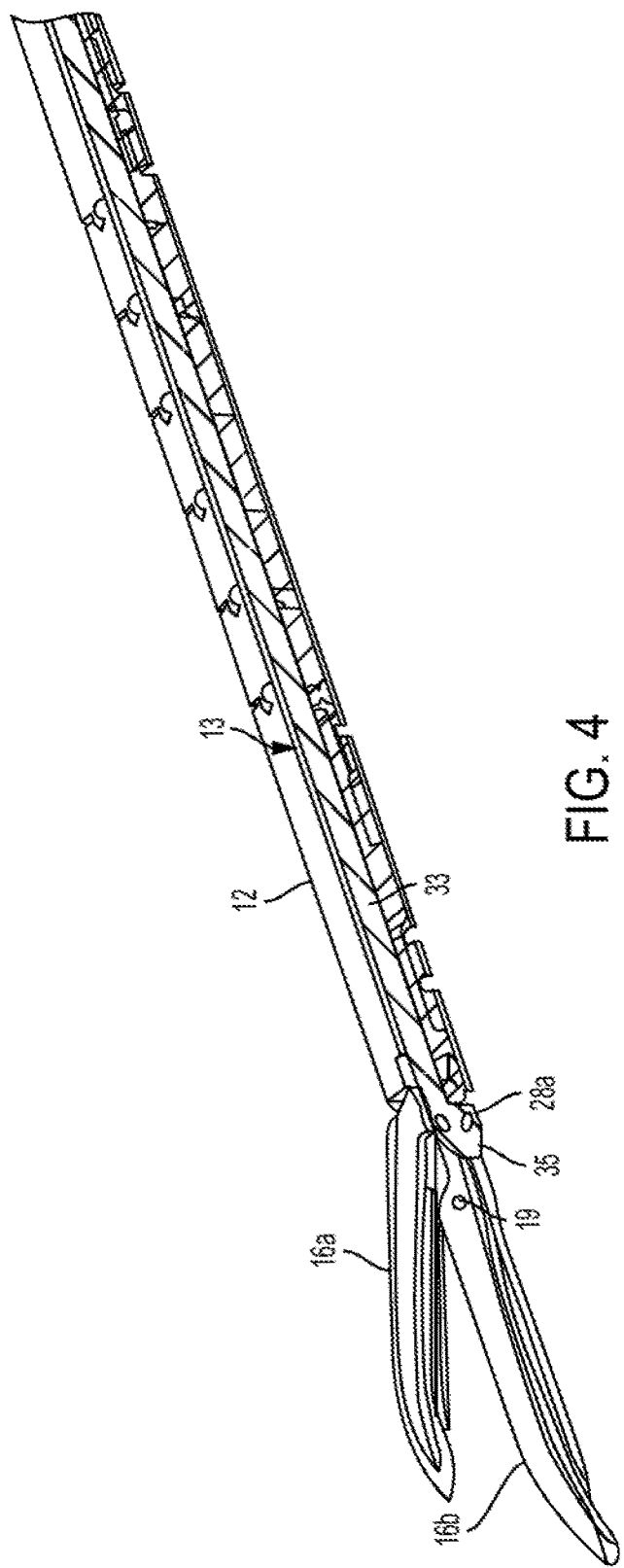
FIG. 4 is a cross-sectional schematic view of the distal portion of the surgical device of FIG. 3.

The jaws 16a, 16b can have any number and any combination of features configured to facilitate sealing tissue between the facing surfaces 18a, 18b of the jaws 16a, 16b. As mentioned above, the sealing of tissue can be effectuated using energy such as RF energy. As in this illustrated embodiment, the end effector 14 can include a plurality of electrodes 19, e.g., opposing polarity conductors, configured to apply energy to tissue clamped by the end effector 14. The electrodes 19 can be on only one of the jaws 16a, 16b or on both of the jaws 16a, 16b. Only one of the electrodes 19 is visible in FIG. 3, but the upper jaw 16a in this illustrated embodiment includes another electrode 19 aligned with the visible electrode 19, and the upper and lower jaws 16a, 16b in this illustrated embodiments includes another pair of electrodes 19 axially aligned with the previously-mentioned electrodes 19 that are on an opposite side of a longitudinal slot 21 formed in and extending along the lower jaw 16b. The other of the lower jaw's electrodes 19 is shown in FIG. 4. Exemplary embodiments of electrodes configured to apply energy to tissue are described in previously mentioned U.S. application Ser. No. 14/166,194 entitled "Surgical Devices Having Controlled Tissue Cutting And Sealing" filed Jan. 28, 2014.

As in this illustrated embodiment, the device 100 can include an activation mechanism 25 configured to activate the electrodes 19 cause the electrodes 19 to apply energy to tissue in contact therewith. The activation button 25 can be operable to selectively activate RF circuitry that is in communication with the end effector 14. In some embodiments, the activation mechanism 25 can be configured as a mechanical lockout against the second movable handle 22, such that the second movable handle 22 cannot be actuated unless the activation mechanism 25 is pressed simultaneously with movement of the second movable handle 22 relative to the first movable and stationary handles 20, 24 as, for example, described in previously mentioned US Pat. Pub. No. 2012/0116379 entitled "Motor Driven Electrosurgical Device With Mechanical And Electrical Feedback" filed Jun. 2, 2011.

One or both of the first and second jaws 16a, 16b can include one or more features configured to interact with a compression member (not shown) configured to apply compressive forces on tissue. For example, the first jaw 16a can include a longitudinal slot (not shown) facing the longitudinal slot 21 of the second jaw 16b that can each receive portions of a compression member and act as a track to direct movement of the compression member. As another example, the first and second recessed slots can be configured to receive portions of a second portion of a cutting element (not shown), as discussed further below.

Figure 5:
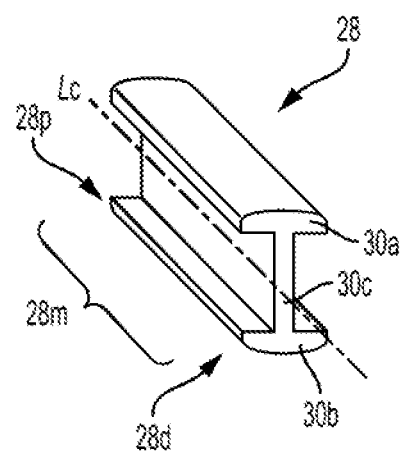
FIG. 5 is a perspective schematic view of one embodiment of a compression member.

The compression member can have various sizes, shapes, and configurations. The compression member can have an elongate shape and can be moveable proximally and distally along the longitudinal axis L1 of the end effector 14. One embodiment of a compression member 28 is illustrated in FIG. 5. As shown, the compression member 28 can have a proximal end 28p, a distal end 28d, and a medial portion 28m extending therebetween. The proximal end 28p and the medial portion 28m of the compression member 28 can be sized and shaped to reciprocate within the shaft portion 12 of the device 100. The distal end 28d of the compression member 28 can be sized and shaped to interact with the jaws 16a, 16b of the end effector 14. A longitudinal axis Lc of the compression member 28 can be parallel to and coaxial with the longitudinal axis L1 of the end effector 14, though other configurations are possible. The compression member 28 can be actuatable from the proximal handle portion 10 of the device 100 by the second movable handle 22, as discussed further below. In general, the second movable handle 22 can be configured to be manually manipulated by a user to cause actuation of one or more other device elements, such as the compression member 28. Other examples of a firing actuator that can actuate the compression member 28 include a lever, a knob, a switch, and a depressible button.

The compression member 28 can include a connecting portion 30c and upper and lower flanges 30a, 30b, thus providing an "I" cross-sectional shape for the compression member 28. As in the illustrated embodiment, the upper and lower flanges 30a, 30b can be positioned substantially perpendicular to the connecting portion 30c to form the "I" cross-sectional shape. The upper and lower flanges 30a, 30b can be sized and shaped to allow the upper and lower flanges 30a, 30b to slide in the longitudinal slot in the upper jaw 16a and in the longitudinal slot 21 of the lower jaw 16b. This sliding contact of lateral edges of the flanges 30a, 30b and sides of each of the longitudinal slots can prevent lateral flexing of the jaws 16a, 16b. The compression member 28 can have various other configurations. For example, the upper flange 30a can have a width that is greater than a width of the lower flange 30b, the widths being measured in a direction perpendicular to the longitudinal axis L1 of the end effector 14.

For another example, the compression member can have a wedge shape, such as in an embodiment of a compression member 28a illustrated in FIG. 4. As in this illustrated embodiment, the compression member 28 can form a distal tip of a drive shaft 33 slidably moveable in the lumen 13 of the shaft 12 that moves through the end effector 14 such that only a distal portion of the drive shaft 13 includes the compression member 28. As in this illustrated embodiment, a longitudinal length of the compression member 28a can be less than the longitudinal length LA of the end effector 14 such that a distal tip of the drive shaft 33 that includes the compression member 28a can move through the end effector 14 without the compression member 28a extending along the entire longitudinal length LA of the end effector 14. Alternatively, the compression member 28a can be along an entire longitudinal length of the drive shaft 33, e.g., the drive shaft 33 can have an "I" shape along its longitudinal length. The compression member 28a can thus extend along the end effector's entire longitudinal length LA when the compression member 28a is in its distal-most position relative to the end effector 14.

The device 100 can include a cutting element (not shown) configured to cut tissue captured between the jaws 16a, 16b. The cutting element can have various sizes, shapes, and configurations. Examples of the cutting element include a knife blade and a sharp edge. The cutting element can be sized and shaped to cut various thicknesses and types of tissue positioned between the jaws 16a, 16b of the end effector 14. As shown in the embodiment illustrated in FIG. 4, a cutting element 35 can be positioned at a distal end of the compression member 28a, such as in this illustrated embodiment by being formed on the compression member 28a as an integral part thereof, e.g., as a sharpened edge thereof, or as a member attached thereto, e.g., a blade mounted thereon. The cutting element 35 can have a sharp or serrated edge configured to transect tissue. In an exemplary embodiment, the cutting element 35 can be recessed relative to distal ends of upper and lower flanges of the compression member 28a that slide within the jaws' longitudinal slots, which can allow compression to occur prior to the cutting element 35 cutting tissue as the compression member 28*a* traverses through the jaws 16*a*, 16*b*. In another embodiment, the cutting element can be configured such that it is not attached to the compression member 28, such that the cutting element can be configured to advance and retract relative to the jaws 16*a*, 16*b* so as to cut tissue sandwiched therebetween without applying compression to the tissue. In this embodiment, the device 100 can include a separate compression member so that tissue engaged by the jaws 16*a*, 16*b* can still be compressed.

Figure 10:
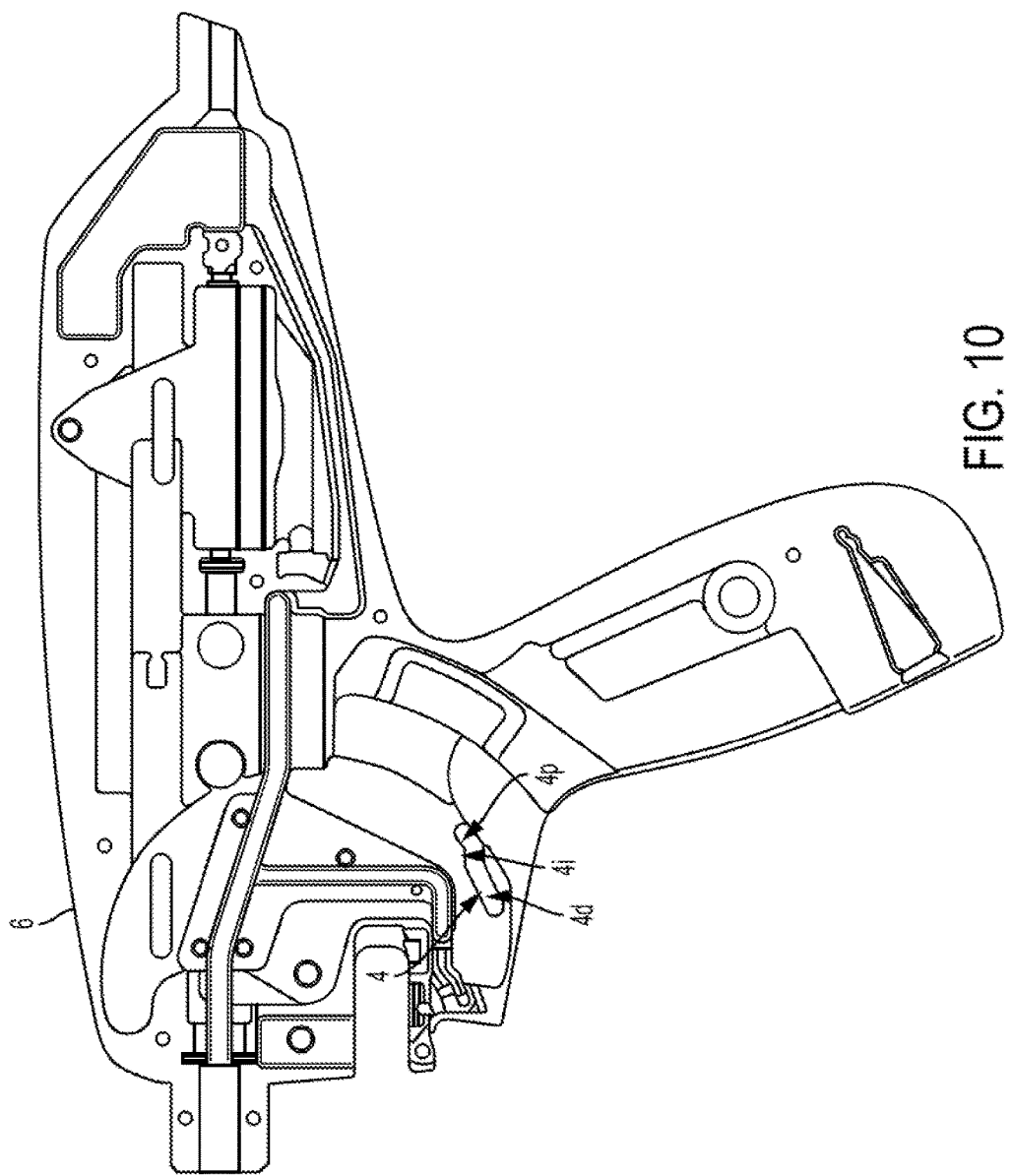
FIG. 10 is a side schematic cross-sectional view of a housing of the surgical device of FIG. 1.
Figure 11:
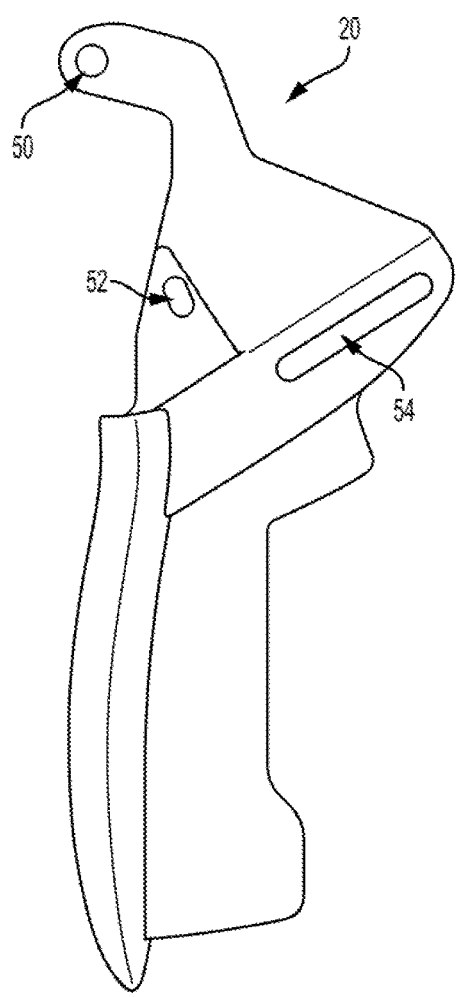
FIG. 11 is a side view of a first movable handle of the surgical device of FIG. 1.
Figure 12:
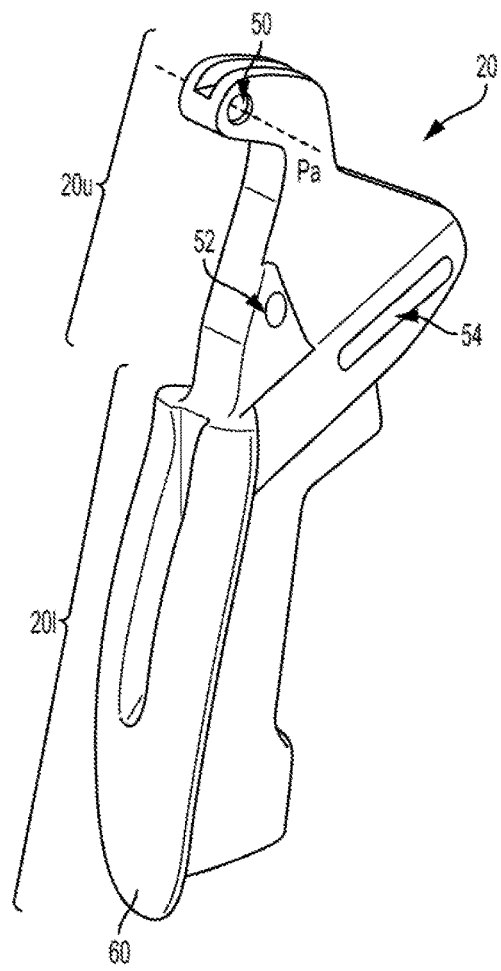
FIG. 12 is a perspective schematic view of the first movable handle of FIG. 11.
Figure 13:
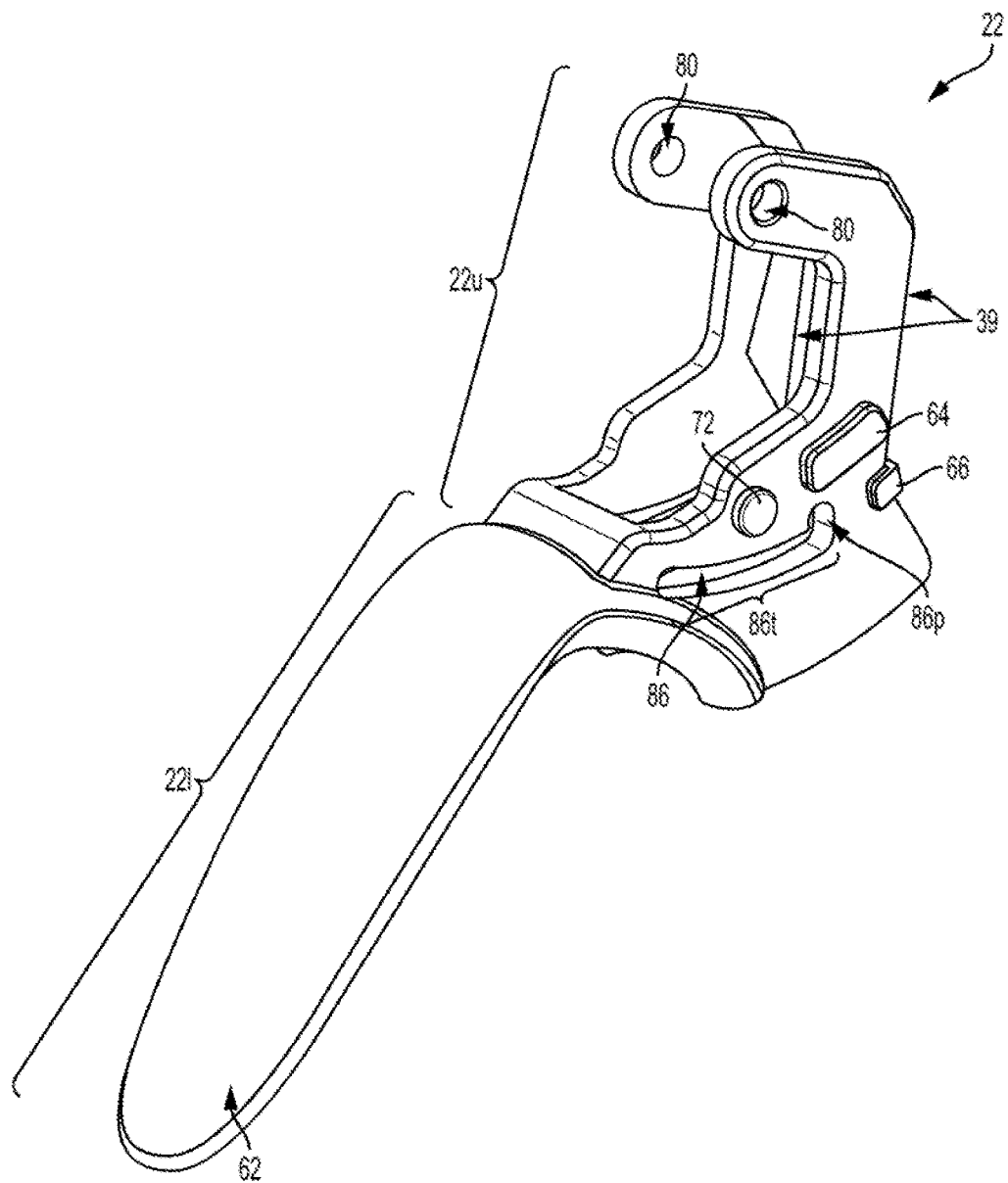
FIG. 13 is a perspective schematic view of a second movable handle of the surgical device of FIG. 1.
Figure 14:
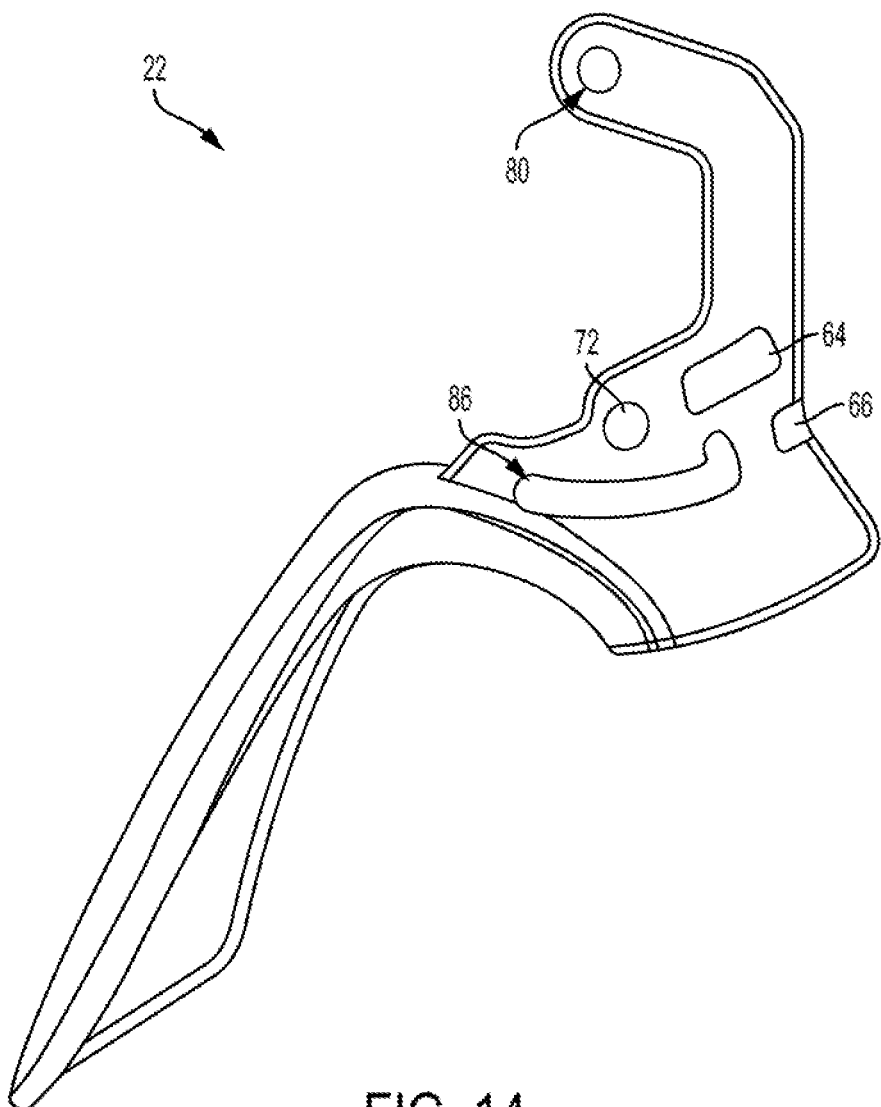
FIG. 14 is a side view of the second movable handle of FIG. 13.
Figure 15:
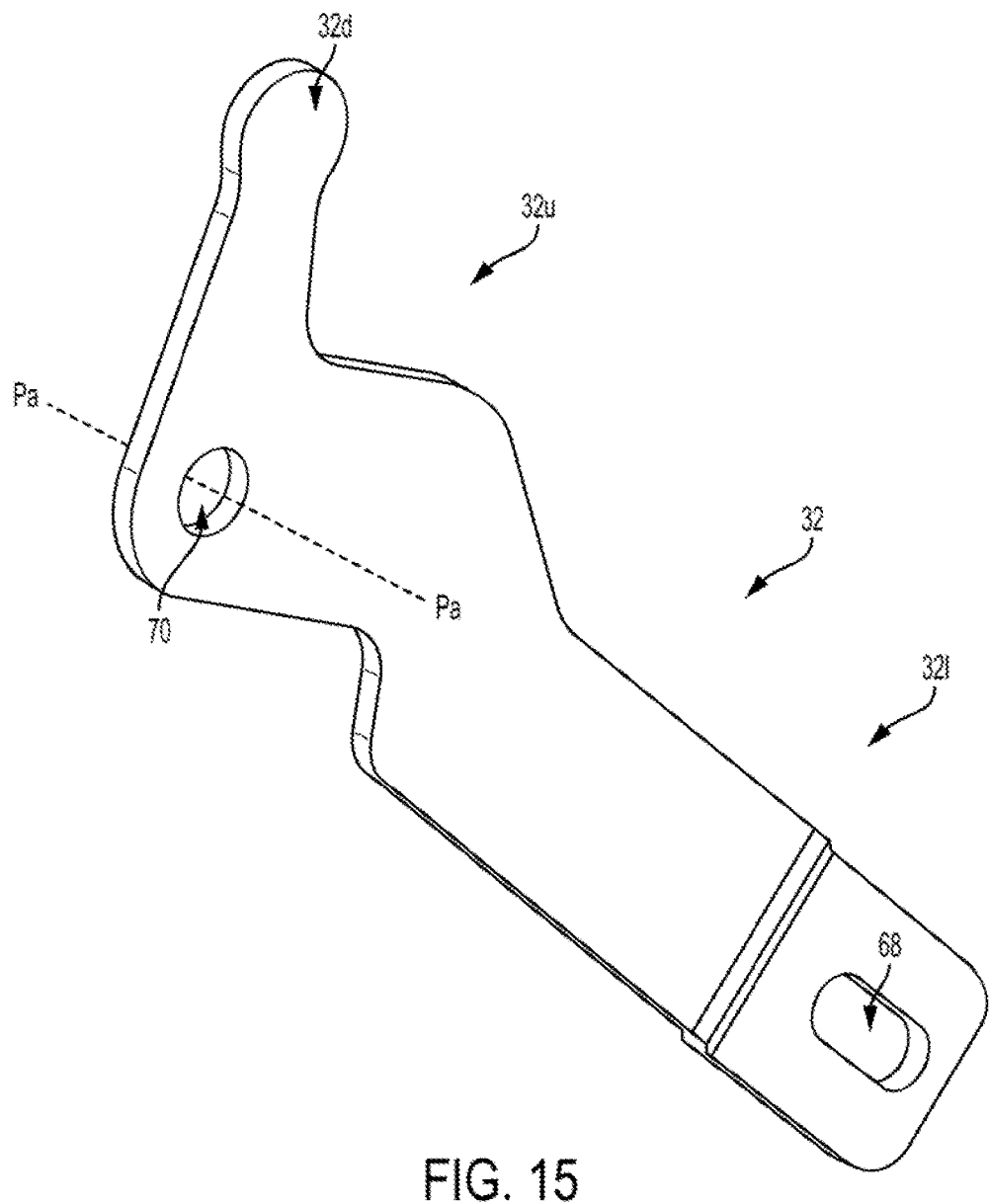
FIG. 15 is a perspective schematic view of a first cam lever of the surgical device of FIG. 1.
Figure 16:
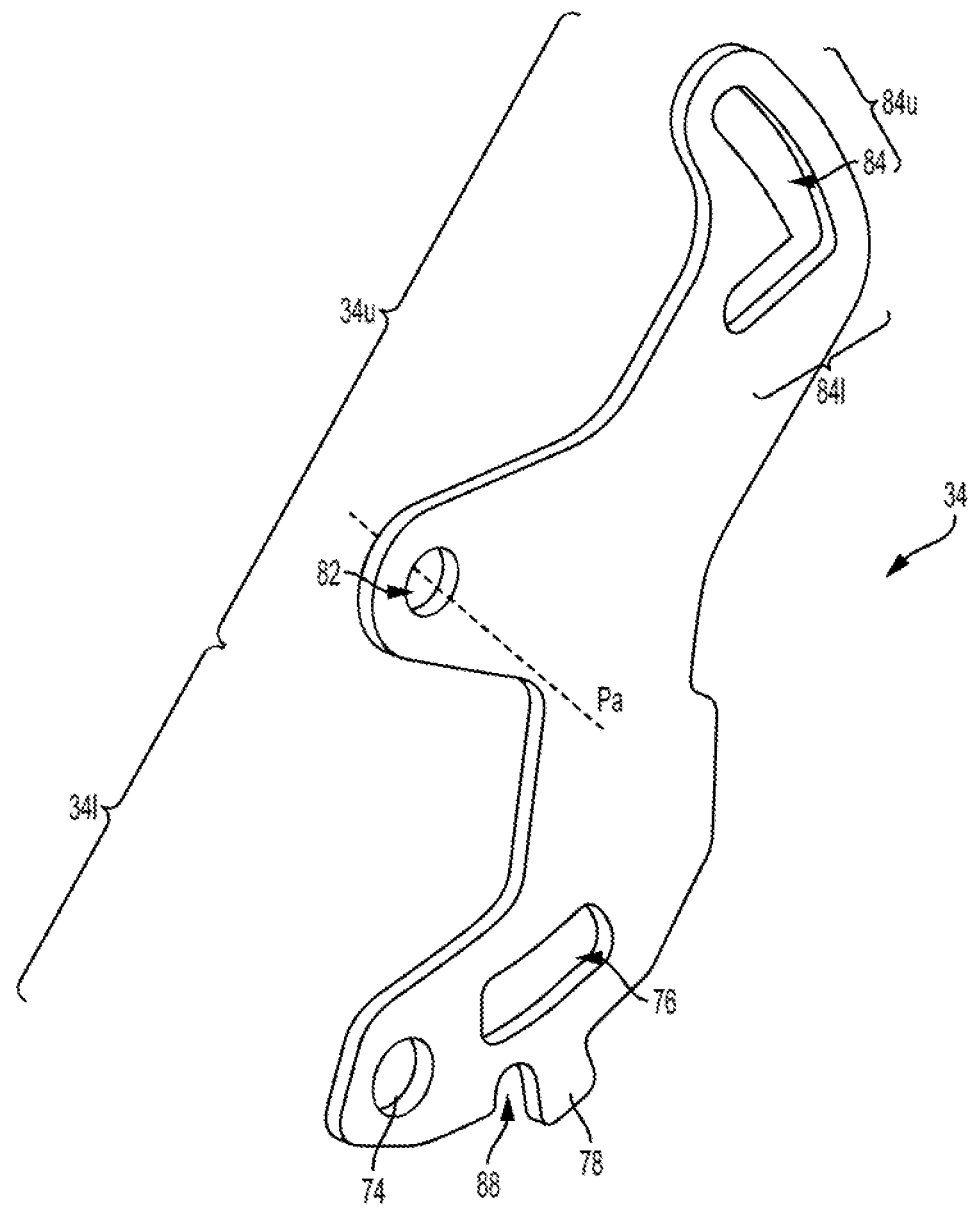
FIG. 16 is a perspective schematic view of a second cam lever of the surgical device of FIG. 1.

As mentioned above, the first and second movable handles 20, 22 can be configured to allow selective firing and closing of the device 100. The first movable handle 20 can be configured to move, e.g., pivot, relative to the stationary handle 24, e.g., to the device's housing 10, to cause the jaws 16*a*, 16*b* of the end effector 14 to move between open and closed positions. The first movable handle 20 can have a first, initial position in which the first movable handle 20 is angularly offset from the stationary handle 24 and in which the jaws 16*a*, 16*b* are open, as shown in FIGS. 1, 2, and 6-9. The first movable handle 20 can have a second, closed position that is different from the initial position and in which the first movable handle 20 is positioned adjacent to or substantially in contact with the stationary handle 24 and in which the jaws 16*a*, 16*b* can engage tissue and apply a force to tissue disposed therebetween. The first movable handle 20 can include a locking feature 20*a*, e.g., a protrusion having a shape, configured to mate with a corresponding locking feature 24*a*, e.g., a recess having a shape configured to fixedly hold the protrusion's shape, of the stationary handle 24 so as to lock the first movable handle 20 in the second position. FIG. 10 illustrates the housing 6 including the stationary handle 24 and the stationary handle's locking feature 24*a*. The first movable handle 20 can have any number of intermediate positions between the initial and closed positions in which the first movable handle 20 is angularly oriented relative to the stationary handle 24 and in which the jaws 16*a*, 16*b* are between the open and closed positions. The first movable handle 20 can be biased to the initial position in which the jaws 16*a*, 16*b* are open. Movement of the first movable handle 20 toward the stationary handle 24, can cause the jaws 16*a*, 16*b* to close, and movement of the first movable handle 20 away from the stationary handle 24, can cause the jaws 16*a*, 16*b* to open. In general, the movement of the first movable handle 20 can cause the shaft 12 to translate longitudinally relative to the end effector 14 as a closure tube so as to effect movement of the upper jaw 16*a* relative to the lower jaw 16*b*.

The second movable handle 22 can be configured to move, e.g., pivot, relative to the stationary handle 24, e.g., to the device's housing 10, to cause the cutting element 35 to translate along the end effector 14, e.g., translate longitudinally therethrough. As in this illustrated embodiment in which the compression member 28*a* is attached to the cutting element 35, the second movable handle's movement can also cause the compression member 28*a* to translate along the end effector 14, e.g., translate longitudinally therethrough by sliding within the jaws' longitudinal slots. The second movable handle 22 can have a first, initial position in which the second movable handle 22 is angularly offset from the stationary handle 24, in which the second movable handle 22 is at a first distance from the first movable handle 20, and in which the cutting element 35 is in a proximal, initial position adjacent proximal ends of the jaws 16*a*, 16*b*, as shown in FIGS. 1, 2, and 6-9. The second movable handle 22 can have a second, ready position in which the first movable handle 20 is in its second, closed position, in which the second movable handle 22 is still at the first distance from the first movable handle 20, and in which the cutting element 35 is still in the proximal, initial position. The second movable handle 22 can have a third, closed position that is different from the initial and ready positions and in which the second movable handle 22 is positioned adjacent to or substantially in contact with the first movable handle 20, in which the second movable handle 22 is at a second distance from the first movable handle 20 that is less than the first distance, and in which the cutting element 35 is in a distal, fired position adjacent distal ends of the jaws 16*a*, 16*b*, e.g., at a distal end of the jaws' longitudinal slots. The second movable handle 22 can have any number of intermediate positions between the initial and ready positions and between the ready and closed position in which the first movable handle 20 is angularly oriented relative to the first movable handle 20 and the stationary handle 24. The second movable handle 22 can be biased to its initial position in which the cutting element 35 is adjacent proximal ends of the jaws 16*a*, 16*b*. Movement of the second movable handle 22 toward the stationary handle 24 can cause the cutting element 35 to move distally relative to the jaws 16*a*, 16*b* so as to cut tissue clamped by the end effector 14 since the cutting element 35 faces in a distal direction, and movement of the second movable handle 22 away from the stationary handle 24 can cause the cutting element 35 to move proximally relative to the jaws 16*a*, 16*b* without cutting any tissue clamped by the end effector 14. In general, the movement of the second movable handle 22 can cause the drive shaft 33 to translate longitudinally, thereby causing translation of the compression member 28*a* and the cutting element 35 fixed thereto.

The first and second movable handles 20, 22 can be configured to be locked in position relative to one another during a first phase of travel in which the first and second movable handles 20, 22 can move simultaneously relative to the stationary handle 24. The first distance between the first and second movable handles 20, 22 can thus be maintained throughout the first phase of travel. The first phase of travel can correspond to the first movable handle 20 moving from its initial position to its closed position and the second movable handle 22 moving from its initial position to its ready position. During the first phase of travel, the first and second movable handles 20, 22 can be configured to move together as a unit. Accordingly, a manual force can be applied to either one or to both of the first and second movable handles 20, 22 to effect movement of the handles 20, 22 in the first phase of travel. In an exemplary embodiment, the manual force can be applied to the second movable handle 22 to effect the simultaneous movement of the first and second movable handles 20, 22, e.g., by a user positioning their palm on the stationary handle 24 and positioning at least one finger on the second movable handle 22 that can be pulled toward the stationary handle 24 to pull both the handles 20, 22 toward the stationary handle 24 due to the fixed positioning of the first and second movable handles 20, 22 relative to one another in the first phase of travel. Such hand positioning can be a natural, comfortable hand position, thereby helping make the device 100 easy and comfortable to use.

A second phase of travel can follow the first phase of travel. The second phase of travel can correspond to the second movable handle 22 moving from its ready position to its closed position. In the second phase of travel, the first movable handle 20 can be configured to remain in its closed position, e.g., in a fixed position relative to the stationary handle 24, and the second movable handle 22 can be configured to move relative to the second movable and stationary handles 20, 24. The second movable handle 24 can thus be unlocked from the first movable handle 22 in the second phase of travel such that the first and second movable handles 20, 22 no longer move in unison in the second phase of travel. A manual force can be applied to the second movable handle 22 to effect the movement of the second movable handle 22 in the second phase of travel. The user's hand can be in the same position on the device 100 during the first and second phases of travel, e.g., with the user positioning their palm on the stationary handle 24 and positioning at least one finger on the second movable handle 22, such that the user need not reposition their hand between the first and second phases of travel. Clamping tissue and cutting tissue can thus be easily and quickly effected by a user during a surgical procedure.

The device 100 can be configured to allow the first and second phases of travel in a variety of ways. As discussed further below, the first movable handle 20, the second movable handle 22, and various components of the device 100 that can be at least partially disposed within the housing 6 can cooperate to allow the first and second phases of travel, as well as the tissue clamping and tissue cutting associated with the first and second phases of travel, respectively.

FIGS. 11-16 illustrate various internal components of the device 100 that can be disposed at least partially within the housing 6, and in particular components of an actuation assembly configured to transfer forces from the first and second movable handles 20, 22 to the end effector 14. While the actuation assembly can have various configurations, in the illustrated embodiment the actuation assembly generally includes the first movable handle 20 (also illustrated in FIGS. 11 and 12), the second movable handle 22 (also illustrated in FIGS. 13 and 14), a first cam lever 32 (also illustrated in FIG. 15) coupled to the first movable handle 20, and a second cam lever 34 coupled to the second movable handle 22 (also illustrated in FIG. 16).

In general, the first movable handle 20 can be configured to move from its initial position toward its closed position, which in turn can cause the first cam lever 32 to rotate and thereby advance the elongate shaft 12 distally. A distal end 32d of the first cam lever 32 can be coupled to the elongate shaft 12, as shown for example in FIGS. 6, 7, and 9, which can allow the movement of the first cam lever 32 to cause a movement of the elongate shaft 12.

A shape of the first movable handle 20 can vary depending on other components of the handle portion 10, but as in the illustrated embodiment, the first movable handle 20 can include an upper portion 20u and a lower portion 20l. The lower portion 20l can be configured to facilitate grasping by a user, such as by including a curved gripping surface 60 configured to receive one or more fingers of a user to facilitate pulling of the first movable handle 20 toward the stationary handle 24. However, as mentioned above, in an exemplary embodiment, a user need not manually manipulate the first movable handle 20 in order to effect movement of the first moveable handle 20. The upper portion 20u can be configured to be disposed within the proximal handle portion 10, e.g., within the housing 6 of the proximal handle portion 10. As in the illustrated embodiment, the upper portion 20u can include a first bore 50 formed therein and configured to seat a first pin 44 therein, a first cam slot 52 formed therein and configured to seat a second pin 46 therein, and a second cam slot 54 formed therein and configured to slidably seat a third pin 56 therein. The second pin 46 can be seated in an upper portion of the first cam slot 52 when the first movable handle is in its initial and intermediate positions and can move to a lower portion of the first cam slot 52 when the first movable handle 20 reaches its closed position. The first cam slot 52 can have a width that prevents the second pin 46 from moving horizontally therein. The first pin 44 can define a trigger pivot axis Pa about which the first movable handle 20 can be configured to rotate under normal load conditions. The first pin 44 can be mounted within the housing 6 to allow pivotal movement of the first movable handle 20 about the trigger pivot axis Pa.

Figure 6:
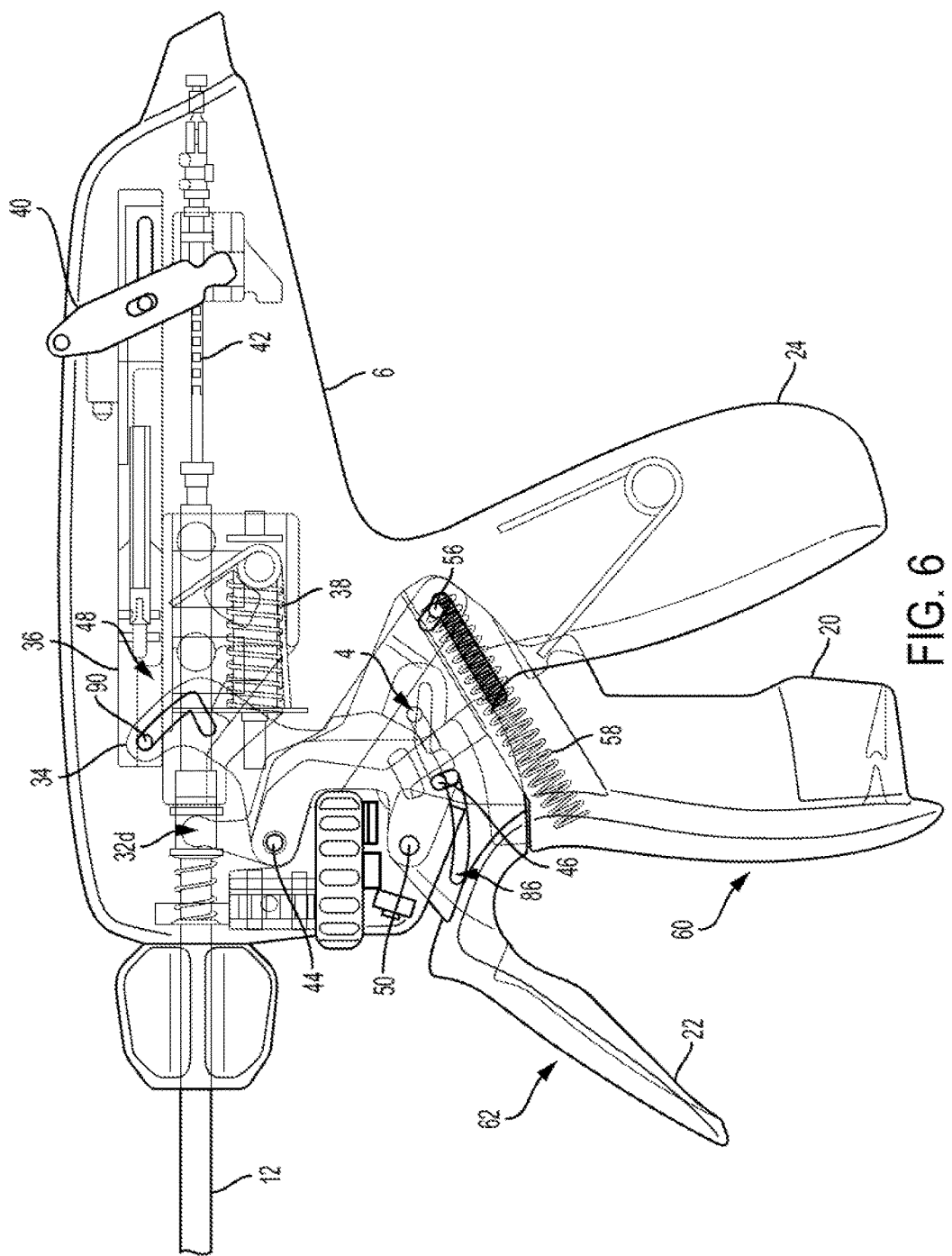
FIG. 6 is a partially transparent cross-sectional side view of a proximal portion of the surgical device of FIG. 1.
Figure 7:
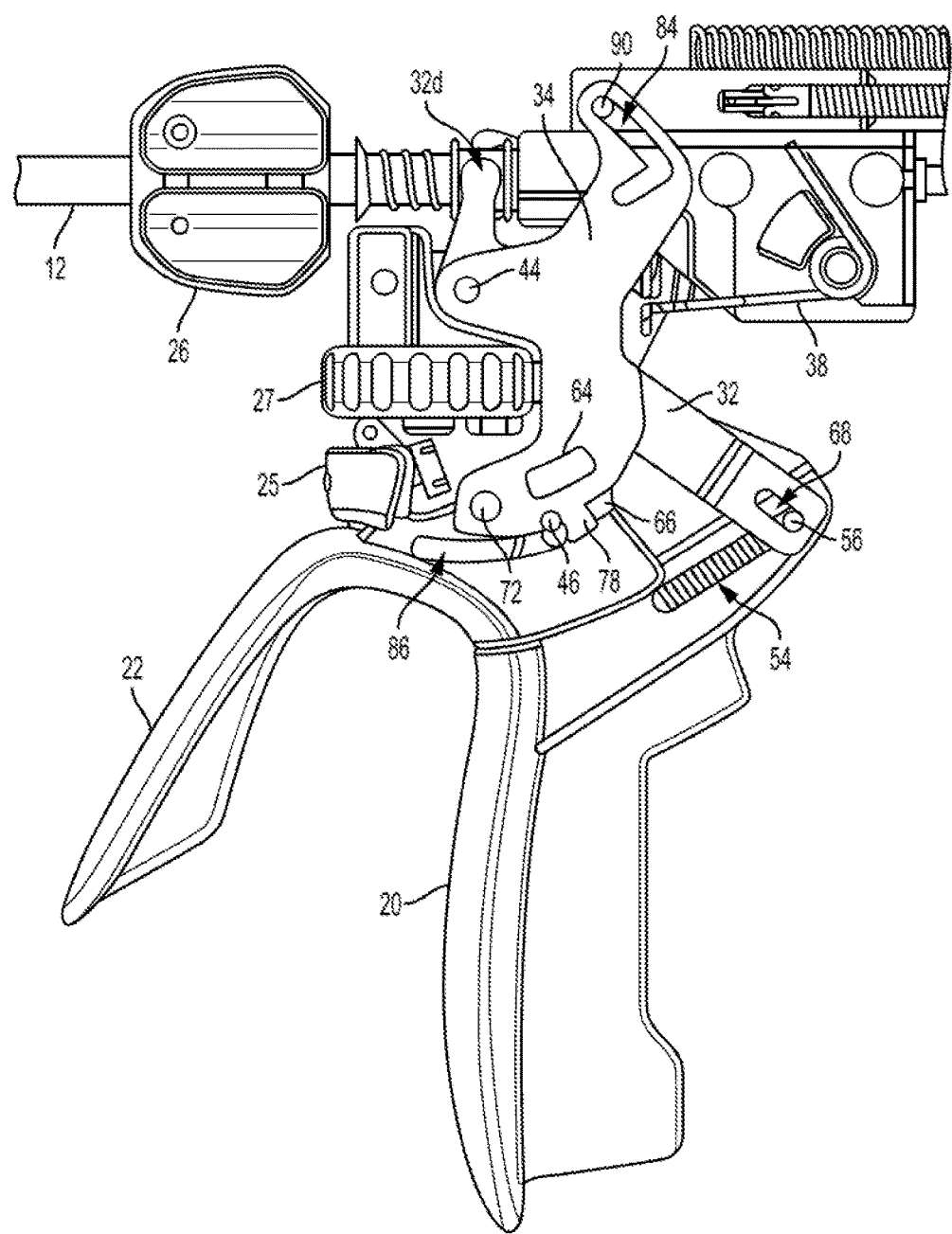
FIG. 7 is a schematic side view of a selection of components in the proximal portion of the surgical device of FIG. 6.
Figure 8:
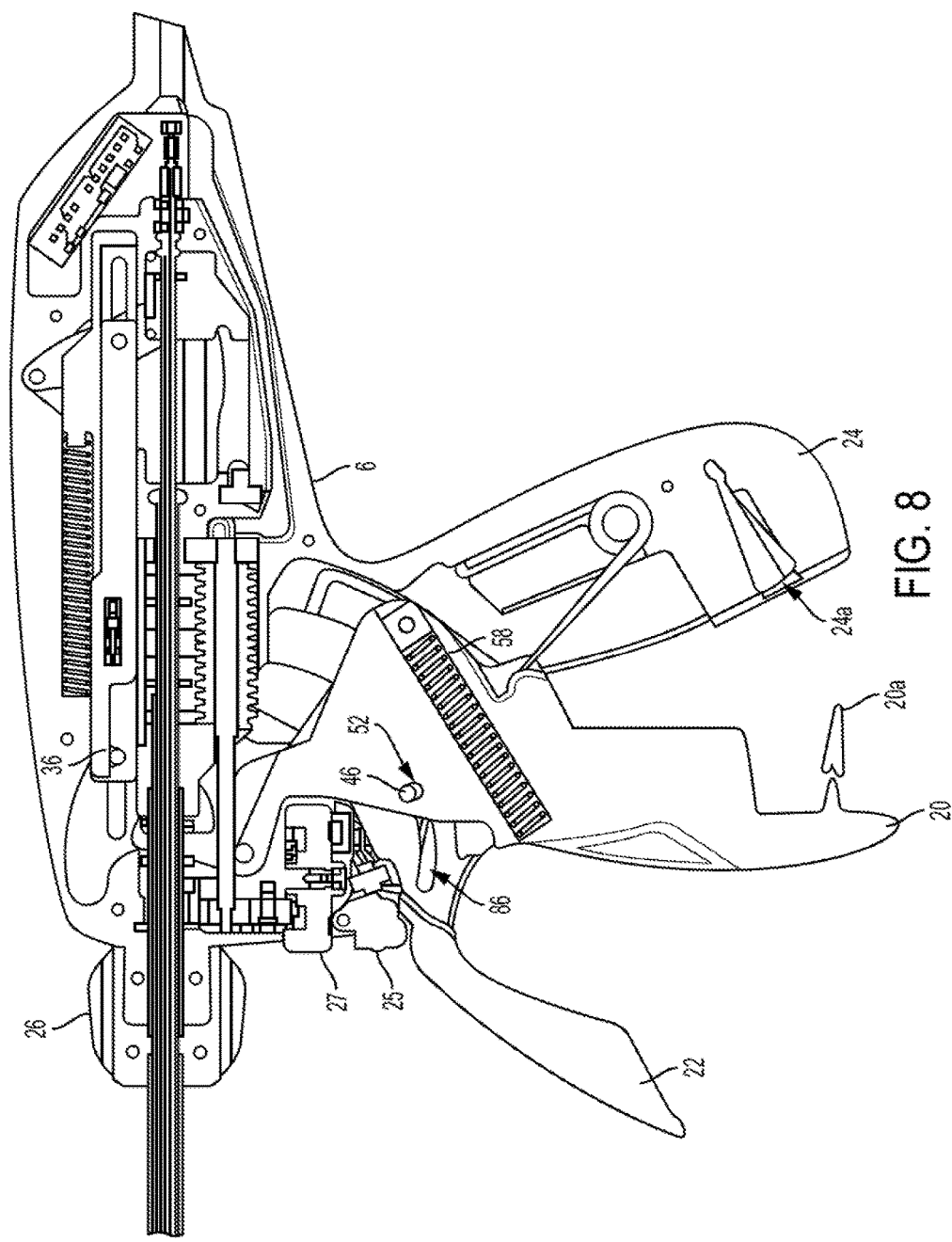
FIG. 8 is a side schematic cross-sectional view of the proximal portion of the surgical device of FIG. 6.
Figure 9:
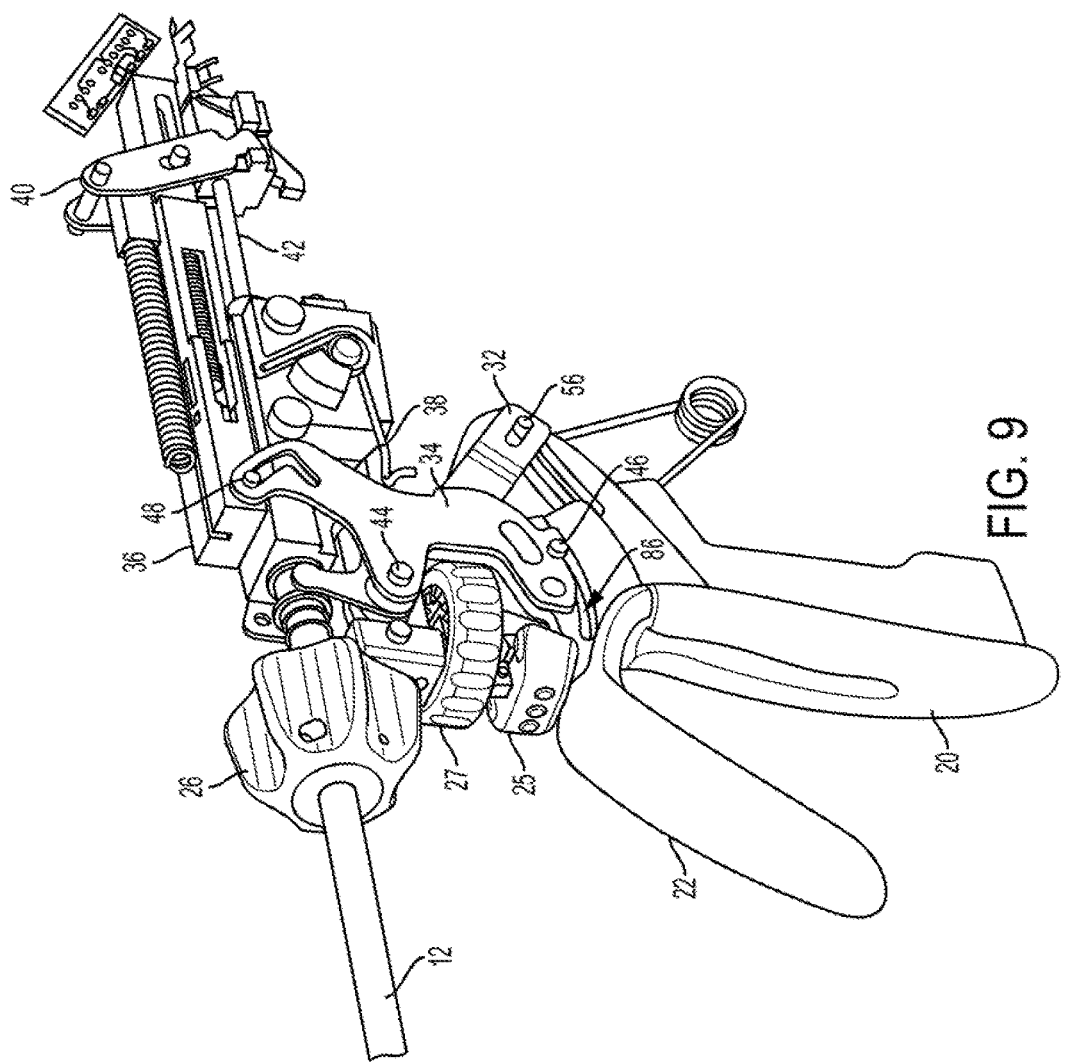
FIG. 9 is a perspective view of a selection of components in the proximal portion of the surgical device of FIG. 6.

The second pin 46 can be configured to be coupled to the housing 6. As shown in FIGS. 6 and 10, the housing 6 can include a third cam slot 4 formed in an interior surface thereof. The third cam slot 4 can be configured to slidably seat the second pin 46 therein. The third cam slot 4 can have a distal, upper portion 4d, a proximal, lower portion 4p, and an intermediate portion 4i angled downward from the upper portion 4d to the lower portion 4p. When the first and second movable handles 20, 22 are in their initial positions, the second pin 46 can be seated at a distal end of the third cam slot 4 in the distal portion 4d, as shown in FIG. 6. During the first phase of travel, the second pin 46 can be configured to slide proximally from its seated position at the third cam slot's distal end within the distal portion 4d of the third cam slot 4, into the intermediate portion 4i of the third cam slot 4, and slide proximally within the intermediate portion 4i of the third cam slot 4. The second pin 46 can thus be positioned at a distal end of the proximal portion 4p of the third cam slot 4 at the end of the first phase of travel when the second movable handle 22 is in its ready position. The second pin 46 can be configured to slide proximally within the distal portion 4d of the third cam slot 4 during the second phase of travel.

A shape of the first cam lever 32 can vary depending on other components of the handle portion 10, but as in this illustrated embodiment, the first cam lever 32 can include an upper portion 32u and a lower portion 32l. The lower portion 32l can be configured to be coupled to the first cam lever 32 via a fourth cam slot 68 formed in the first cam lever 32. The third pin 56 slidably seated in the first movable handle's second cam slot 54 can be configured to be slidably seated in the first cam lever's fourth cam slot 68. Accordingly, movement of the first movable handle 20 can cause the third pin 56 to slide within the fourth cam slot 68 to translate a bias force exerted by the first spring 58 into a rotational force applied to the first cam lever 32. The first cam lever 32 can include a third bore 70 formed therein and configured to seat the first pin 44 therein. Accordingly, the first cam lever 32 can be configured to rotate about the trigger pivot axis Pa defined by the first pin 44.

A first biasing element 58 at the proximal handle portion 10 can be configured to bias the first movable handle 20 to its initial position. A force applied to the first movable handle 20, e.g., a manual force applied by the user to the first movable handle 20 during the first phase of travel, can be adequate force to overcome the biasing force applied by the first biasing member, thereby allowing the first movable handle 20 to pivot about the trigger pivot axis and move from its first position toward its second position.

In general, the second movable handle 22 can be configured to move from its initial position toward its ready position in the first phase of travel, which in turn can cause the second cam lever 34 to rotate until a second biasing element 38 moves into contact with a surface 39 of the second movable handle 22 when the second movable handle 22 reaches the ready position so as to begin applying a force to the second movable handle 22. Movement of the second movable handle 22 from its ready position to its closed position in the second phase of travel can cause the second cam lever 34 to rotate, e.g., to continue rotating in the same direction as during the first phase of travel, which in turn can cause the second biasing element 38 to rotate and slide along the surface 39, and can cause a firing bar 36 to advance distally. The force applied by the second biasing element 38 can decrease as the second movable handle 22 rotates, thereby making it easier for a user to overcome that force and cause the cutting element's translation through the end effector 14. The second movable handle's surface 39 can be angled in a distal direction when the second biasing element 38 slides therealong to allow the force to decrease. The distal movement of the firing bar 36 can cause a cam member 40 coupled to the firing bar 36 to rotate, e.g., in a direction opposite to the rotation of the second cam lever 34. The rotation of the cam member 40 can cause a firing rod 42 coupled to the cam member 40 to move distally. A distal end (not shown) of the firing rod 42 can be coupled to a proximal end (not shown) of the drive shaft 33 such that the distal movement of the firing rod 42 can cause the drive shaft 33, and hence the cutting element 35 and compression member 28a coupled thereto, to move distally relative to the end effector 14.

A shape of the second movable handle 22 can vary depending on other components of the handle portion 10, but as in the illustrated embodiment, the second movable handle 22 can include an upper portion 22u and a lower portion 22l. The lower portion 22l can be configured to facilitate grasping by a user, such as by including a curved gripping surface 62 configured to receive one or more fingers of a user to facilitate pulling of the second movable handle 22 toward the stationary handle 24 and, in the second phase of travel, also toward the first movable handle 20. The upper portion 22u can be configured to be disposed within the proximal handle portion 10, e.g., within the housing 6 of the proximal handle portion 10. As in the illustrated embodiment, the upper portion 22u can include a fourth bore 80 formed therein and configured to seat the first pin 44 therein. Accordingly, the second movable handle 22 can be configured to rotate about the trigger pivot axis Pa defined by the first pin 44. Also as in the illustrated embodiment, the upper portion 22u can include a fifth cam slot 86 formed therein and configured to slidably seat the second pin 46 therein, a fourth pin 72 configured to couple the second movable handle 22 with the second cam lever 34, a first coupling member 64 (e.g., a protrusion extending from a surface thereof) configured to couple the second movable handle 22 with the second cam lever 34, and a first engagement member 66 configured to engage the second cam lever 34 and to facilitate movement of the second pin 46 within the fifth cam slot 86. The first cam slot 52 formed in the first movable handle 20 can cooperate with the fifth cam slot 86 and the second pin 46 to lock the first and second movable handles 20, 22 in a fixed position relative to one another when the first and second movable handles 20, 22 are in their initial positions and during the first phase of travel. The first cam slot 52 can extend vertically, e.g., top to bottom, so as to allow the second pin 46 to slide vertically therein, as discussed above when the second pin 46 moves to the lower portion of the first cam slot 52.

The fifth cam slot 86 can include a lower, travel portion 86t and a upper, protruding portion 86p that protrudes to a side of the travel portion 86t so as to be offset therefrom. The protruding portion 86p can define a locking cut-out of the fifth cam slot 86 in which the second pin 46 can be seated prior to its sliding movement within the travel portion 86t. The second pin 46 can be seated within the protruding portion 86 when the second movable handle 22 is in its initial position and, thus, during the first phase of travel. The protruding portion 86p can thus facilitate locking of the second movable handle 22 in a stationary position relative to the first movable handle 20 during the first phase of travel since the second pin 46 can be seated in the first movable handle's first cam slot 52 and in the second movable handle's protruding portion 86p of the fifth cam slot 86. The travel portion 86t can define an elongate path along which the second pin 46 can freely slide during the second phase of travel.

A shape of the second cam lever 34 can vary depending on other components of the handle portion 10, but as in this illustrated embodiment, the second cam lever 34 can include an upper portion 34u and a lower portion 34l. The lower portion 34l can be configured to be coupled to the second movable handle 22. The second cam lever's lower portion 34l can include a fifth bore 74 formed therein, a cut-out 76 formed therein, a second engagement member 78 (e.g., a protrusion extending from the second cam lever's surface), and a notch 88 formed therein that can each be configured to facilitate the second cam lever's coupling to the second movable handle 22. The fifth bore 74 can be configured to seat the fourth pin 72 extending from the second movable handle 22 therein. The cut-out 76 can be configured to seat therein the protrusion 64 extending from the second movable handle 22, which can facilitate secure coupling of the second cam lever 34 and the second movable handle 22. The second engagement member 78, e.g., a proximal side thereof, can be configured to abut the first engagement member 66, e.g., a distal side thereof. This engagement of the first and second engagement members 66, 78 can allow the second movable handle 22 and the second cam lever 34 to rotate together by the second engagement member 78 pushing against the first engagement member 66. The second engagement member 78 and the notch 88 can cooperate to facilitate the locking and the movement of the second pin 46 within the fifth cam slot 86 formed in the second movable handle 22. The notch 88 can be configured to seat the second pin 46 therein when the second pin 46 is seated in the protruding portion 86p of the fifth cam slot 86. In other words, the second pin 46 can be seated in the notch 88 when the second movable handle 22 is in its initial position and during the first phase of travel. The second movable handle 22 moving to its ready position at the end of the first phase of travel can cause the second pin 46 to move from being within the notch 88 and within the protruding portion 86p to being adjacent the second engagement member 78 on a distal side thereof and being within the fifth cam slot's travel portion 86t in a proximal portion thereof.

The second cam lever's upper portion 34u can include a sixth bore 82 configured to seat the first pin 44 therein. Accordingly, the second cam lever 34 can be configured to rotate about the trigger pivot axis Pa defined by the first pin 44. The upper portion 34u can also include a sixth cam slot 84 formed therein. The sixth cam slot 84 can have an "L" shape and can include a first, upper leg 84u defining a longer leg of the "L" shape and a second, lower leg 84l defining a shorter leg of the "L" shape. The sixth cam slot 84 can be configured to slidably seat therein a fifth pin 90 therein that can extend from an interior surface of the housing 6. The fifth pin 90 can also extend through an opening 48 formed in the firing bar 36. The fifth pin 90 can be configured to be seated in an upper portion of the upper leg 84u and in a distal portion of the opening 48 when the first and second movable handles 20, 22 are in their initial positions. The fifth pin 90 can be configured to remain stationary within the opening 48 and to slide within the upper leg 84u down toward the lower leg 84l during the first phase of travel. At the end of the first phase of travel when the first movable handle 20 is in its closed position and the second movable handle 22 is in its ready position, the fifth pin 90 can remain stationary within the opening 48 and can be located within the sixth cam slot 84 just above a junction between the upper and lower legs 84u, 84l, e.g., at the bend of the "L" shape. During the second phase of travel, the fifth pin 90 can be configured to remain stationary within the opening 48, and can be configured to slide within the lower leg 84l in a direction away from the upper leg 84u. The sixth cam slot 84 can thus be configured to help prevent firing of the cutting element 35 during the first phase of travel by helping prevent distal movement of the firing bar 36 during the first phase of travel due to the position of the fifth pin 90 within the opening 48 and the sixth cam slot 84.

The device 100 of FIG. 1 can be operated using manual power without the need for any electrical power supplied thereto. In some embodiments, a surgical device configured to clamp and cut tissue and including first and second movable handles can be a powered device that uses electrical power to effect one or more actions. Such powering can be implemented in a variety of ways, as will be appreciated by a person skilled in the art.

For example, a powered surgical device can include a motor, a controller, and a power source. The motor, the controller, and/or the power source can be at least partially disposed in a proximal handle portion of the device. As will be appreciated by a person skilled in the art, the motor can include any type of motor (e.g., a rotary motor, etc.) configured for use with a surgical device, the controller can include a variety of devices configured to process signals (e.g., a microprocessor, a central processing unit (CPU), a memory controller, etc.), and the power source can include a variety of devices configured to supply power to at least the controller (e.g., a battery, etc.). In some embodiments, the power source can be off-board, e.g., entirely outside the device's housing, instead of on-board the device, such as by the device being attachable via wired connection to an electrical outlet or other power source. A manual movement of the device's first movable handle can be configured to cause the controller to transmit a control signal to the motor, which can cause opposed jaws of the device to close. The device's second movable handle can be in electrical communication with the motor. The motor can be operatively coupled to the compression member using e.g., a gear and rack. In some embodiments, activation of the motor can cause advancement and/or retraction of the compression member.

The surgical devices disclosed herein can be used to perform a surgical procedure in which tissue is grasped and transected. The tissue can include, for example, stomach tissue, intestinal tissue, esophageal tissue, or blood vessels. The surgical procedure can be a minimally invasive procedure or an open surgical procedure. The surgical devices disclosed herein can be used in robotic-assisted minimally invasive or open surgical procedures.

For example, a minimally invasive surgical procedure can begin by preparing the patient for surgery and making one or more appropriately sized incisions at a desired location. This general example is described with respect to the surgical device 100 of FIG. 1, but other embodiments of devices described herein can be similarly used. In a minimally invasive procedure, one or more cannulas or trocars (not shown) can be positioned in the incision(s) to provide access to the surgical site. One or more viewing devices, e.g., scopes, can be placed in one of the incisions to allow medical personnel to view the surgical site from outside the body.

Once the patient is prepared for surgery, the surgical device 100 can be inserted through an incision and/or through a cannula, and the end effector 14 of the surgical device 100 can be positioned adjacent to a desired tissue to be treated. As the surgical device 100 is being inserted into the patient, the first movable handle 20 can be disposed adjacent to the stationary handle 24 so that the end effector 24 is in a closed position and occupies a smaller amount of space than when in an open position. As discussed above, such movement of the first movable handle 14 to close the jaws 16a, 16b of the end effector 14 can simultaneously move the second movable handle 22. When the end effector 14 is positioned adjacent to the tissue to be treated, the first movable handle 20 can be moved away from the stationary handle 24 if so positioned for ease of insertion into the patient's body, and the tissue to be treated can be positioned between the facing engagement surfaces 18a, 18b of the end effector's jaws 16a, 16b.

With the target tissue positioned between the facing engagement surfaces 18a, 18b of the end effector's jaws 16a, 16b, and the first and second movable handles 20, 22 in their initial positions, as shown in FIGS. 6-9, the first movable handle 20 can be moved toward the stationary handle 24 in a first phase of travel. As mentioned above, the movement of the first movable handle 20 in the first phase of travel can also include movement of the second movable handle 22 in unison with the first movable handle 20. Indeed, as also mentioned above, the first movable handle 20 need not be manually held by a user at all in order to effect movement of the first movable handle 20 since the first and second movable handles 20, 22 can be locked in position relative to one another in their initial positions at the start of the first phase of travel such that manual movement of the second movable handle 22 can cause the first movable handle 20 to move in unison therewith. The first movable handle's movement from its initial position in the first phase of travel can close the jaws 16a, 16b so that the engagement surfaces 18a, 18b are in direct contact with the tissue and so that the tissue is securely grasped between the jaws 16a, 16b. A position of the jaws 16a, 16b throughout the first phase of travel can directly correspond to a position of the first movable handle 20 relative to the stationary handle 24.

Figure 17:
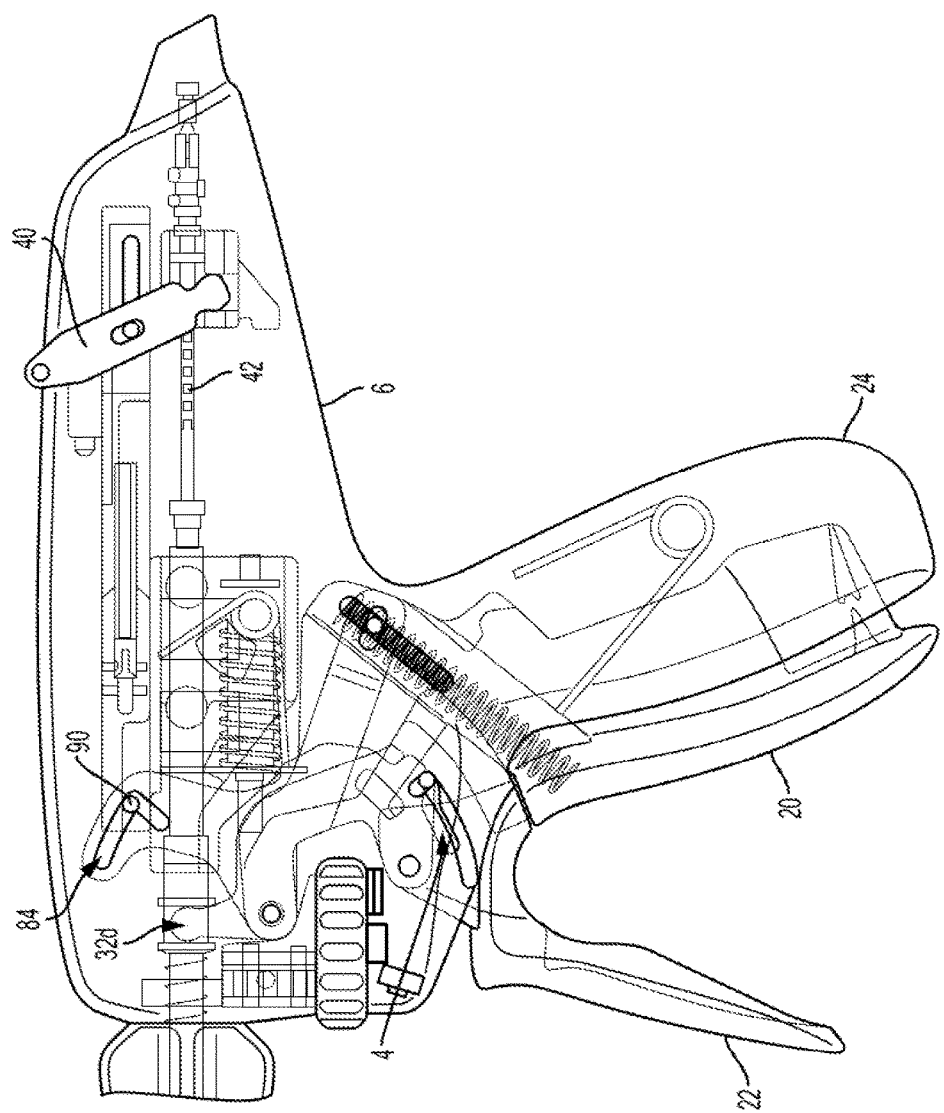
FIG. 17 is a partially transparent cross-sectional side view of the proximal portion of the surgical device of FIG. 6 with the first movable handle moved to a closed position.
Figure 18:
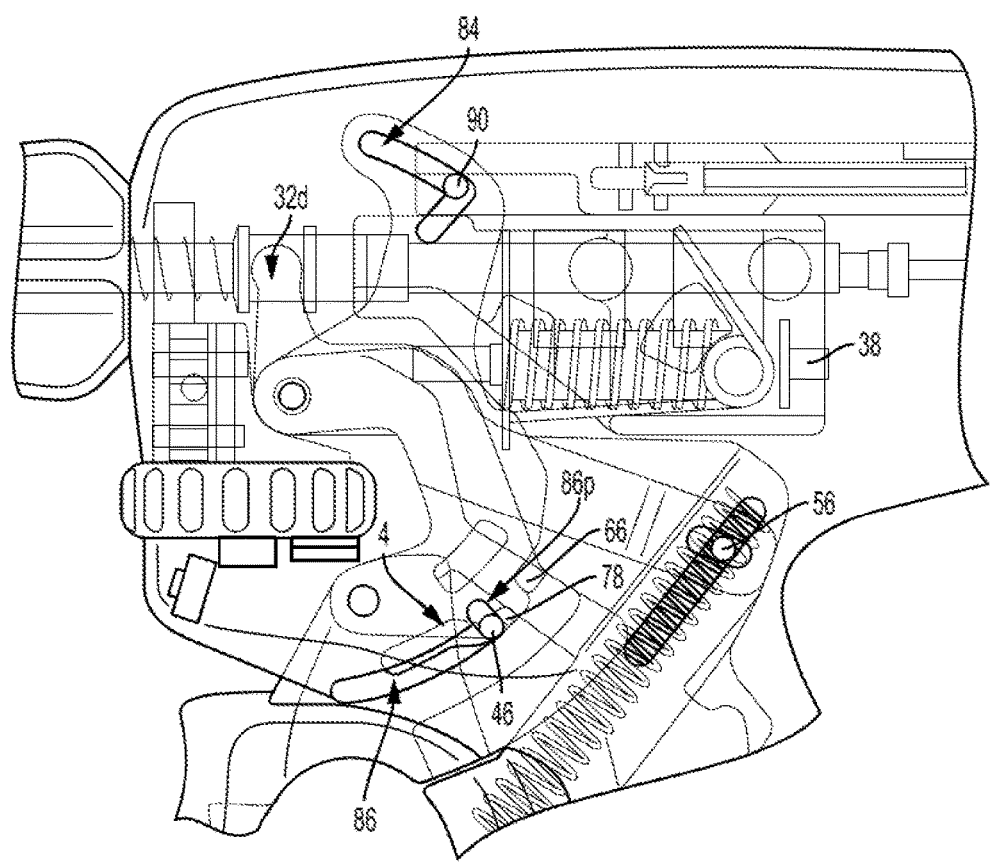
FIG. 18 is a partially transparent cross-sectional side view of a portion of the surgical device of FIG. 17.

FIGS. 17 and 18 show the device 100 at the end of the first phase of travel with the first movable handle 20 in its closed position in which it is locked in position via engagement of the locking features 20a, 24a, and with the second movable handle 22 in its ready position. In the ready position, the second movable handle's surface 39 has moved into contact with the second biasing element 38 to provide a bias force to the second movable handle 22. This bias force can hold the second movable handle 22 in the ready position until a force is applied to the second movable handle 22 to overcome the bias force, e.g., until the user applies a manual force to the second movable handle 22 that is greater than the bias force. The movement of the second pin 46 during the first phase of travel within the third cam slot 4 formed in the device's body portion 6 moves the second pin 46 downward as the second pin 46 moves downward in the angled intermediate portion 4i of the third cam slot 4. This downward movement of the second pin 46 can cause the second pin 46 to move out of the upper portion 86p of the fifth cam slot 86 and into the lower portion 86t of the fifth cam slot 86, thereby allowing the second movable handle 22 to move in the second phase of travel toward the first movable handle 20 and the stationary handle 24 and allowing the cutting element 35 to move during the second phase of travel. In other words, the second pin 46 has become unlocked with respect to the second movable handle 22 by ceasing to be locked within the protruding portion 86p of the fifth cam slot 86 formed in the second movable handle 22. The cutting element 35 thus cannot move along the end effector 14 to cut tissue grasped thereby until the first movable handle 20 is in its closed position such that the end effector 14 has been closed to clamp tissue. This can improve safety by helping to prevent premature cutting of tissue and/or helping to prevent the cutting element 35 from moving along the end effector 14 and cutting material (e.g., tissue other than the target tissue, another surgical instrument, etc.) positioned between the jaws 16a, 16b that is not intended to be cut. During the first phase of travel, the fifth pin 90 can be located within the upper leg 84u of the sixth cam slot 84 just above the junction between the upper and lower legs 84u, 84l such that the fifth pin 90 cannot slide within the lower leg 84l until the bias force is overcome, thereby further rotating the second cam lever 34 so as to move the fifth pin 90 into the lower leg 84l.

Figure 19:
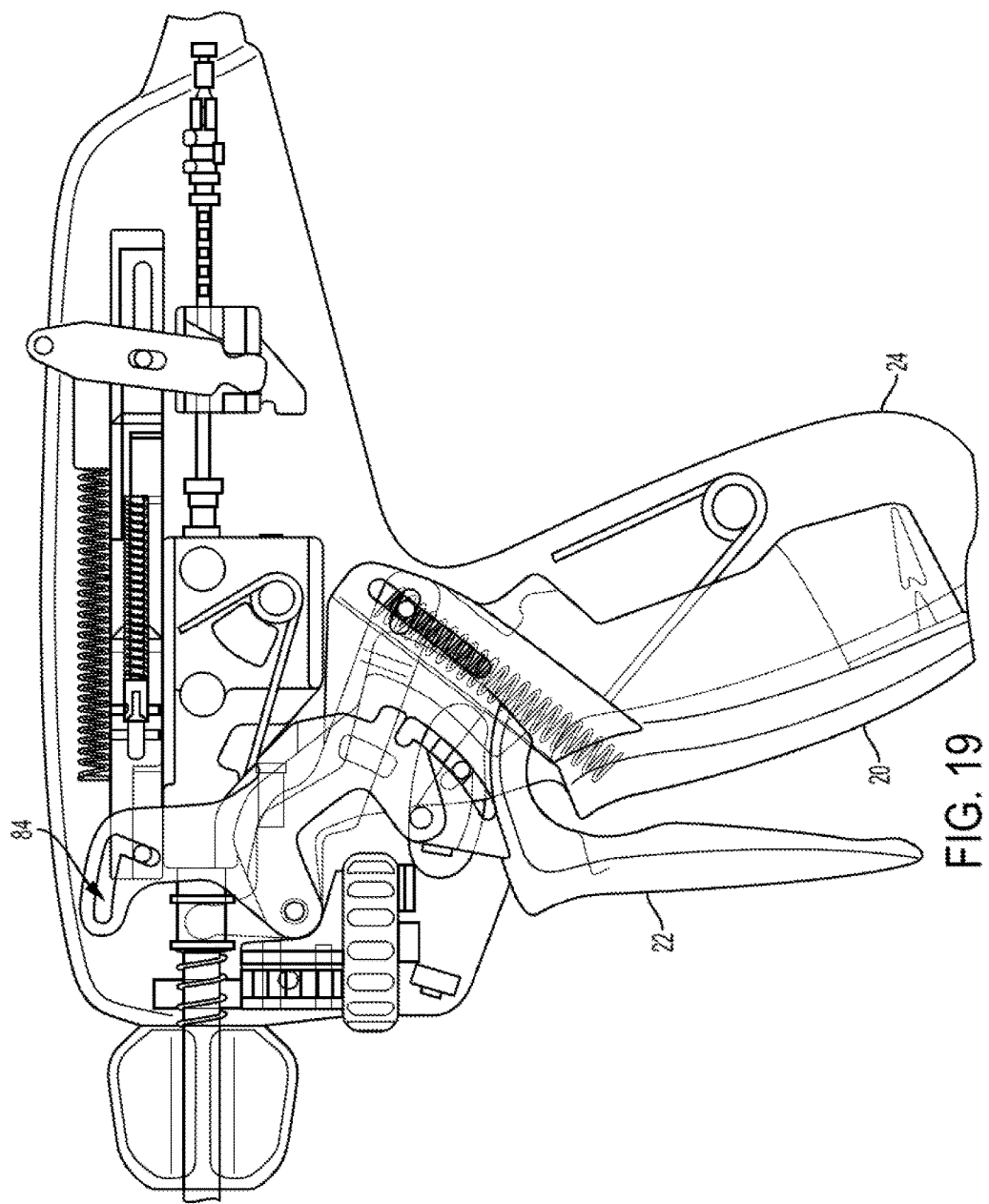
FIG. 19 is a partially transparent cross-sectional side view of the proximal portion of the surgical device of FIG. 17 with the second movable handle in an intermediate position.
Figure 20:
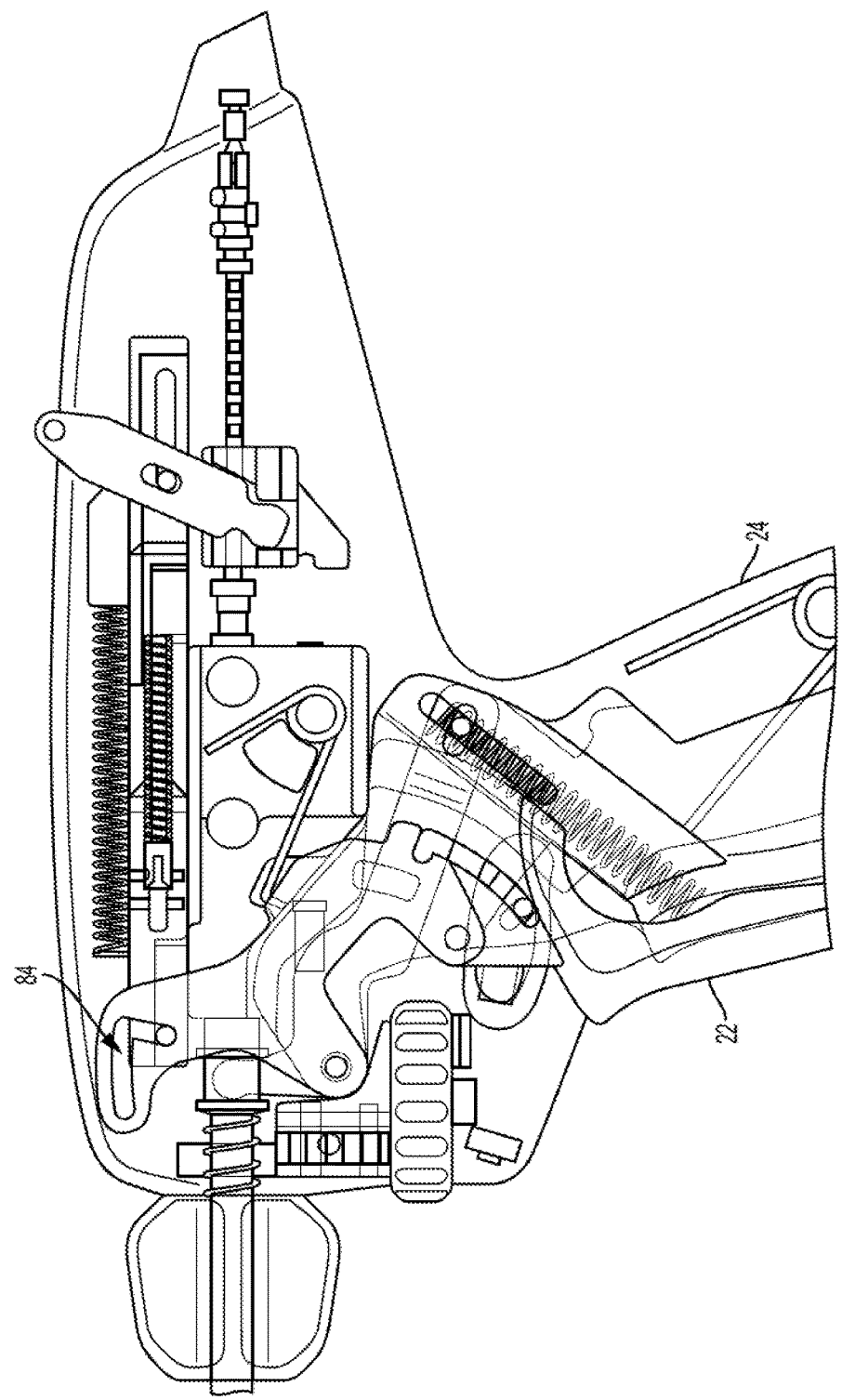
FIG. 20 is a partially transparent cross-sectional side view of the proximal portion of the surgical device of FIG. 19 with the second movable handle in a closed position.

With the jaws 16a, 16b having tissue grasped therebetween, a user can move the second movable handle 22 in a second phase of travel, which can advance the cutting element 35 to cut the grasped tissue and/or advance the compression member 28a to further compress the grasped tissue. FIG. 19 shows the device 100 during the second phase of travel with the second movable handle 22 being in an intermediate position between its ready and closed positions. FIG. 20 shows the device 100 at the end of the second phase of travel with the second movable handle 22 in its closed position. The second movable handle 22 can be configured to be locked in its closed position due to the second pin's position within the third cam slot 4, the second bore 56, and the fifth cam slot 86.

After the second phase of travel, with the first and second movable handles 20, 22 in their closed positions, the first movable handle 20 can be unlocked from the stationary handle 24 by moving the first movable handle 20 in a direction toward the stationary handle 24, e.g., by applying a manual force to the first movable handle 20, thereby causing the locking features 20a, 24a to disengage. This unlocking can release both the first and second movable handles 20, 22 from the stationary handle 24 to allow both the first and second movable handles 20, 22 to move in reverse, e.g., away from the stationary handle 24, back to their initial positions. The device 100 can then be used to clamp and/or cut additional tissue, if desired, before the device 100 is removed from the patient's body.

A person skilled in the art will appreciate that, optionally, energy can be applied to the tissue prior to or during the cutting of the tissue between the jaws 16a, 16b, e.g., during the second phase of travel, by actuating the activation element 25 of the device 100. After the cutting element 35 is advanced through the tissue and is retracted proximally, the device 100 can continue to apply energy to the cut tissue, or the jaws 16a, 16b can automatically release the tissue.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
  a proximal handle portion including a stationary handle, a first movable handle, and a second movable handle, the second movable handle being locked to the first movable handle during a first phase of travel from a first initial position to a second, intermediate position such that the first and second movable handles move together as a unit toward the stationary handle during the first phase of travel, the second movable handle being unlocked from the first movable handle during a second phase of travel from the second position to a third, final position;
  an elongate shaft extending distally from the handle portion;
  first and second jaws at a distal end of the elongate shaft, the first and second jaws being configured for relative movement between an open position and a closed position, the first and second jaws being configured to move from the open position to the closed position during the first phase of travel; and
  a cutting element configured to move through the first and second jaws so as to cut tissue engaged by the first and second jaws in response to the second movable handle moving toward the stationary handle during the second phase of travel.

2. The device of claim 1, wherein the first movable handle in the second position is locked in position relative to the stationary handle, the first movable handle remaining in the locked position during the second phase of travel.

3. The device of claim 1, further comprising one or more electrodes coupled to at least one of the first and second jaws, the one or more electrodes being configured to apply radiofrequency (RF) energy to the tissue engaged by the first and second jaws.

4. The device of claim 1, further comprising a spring disposed within the proximal handle portion, the spring being configured to apply a bias force to the second movable handle to hold the second movable handle in a fixed position after the first phase of travel, the movement of the second movable handle during the second phase of travel being configured to overcome the bias force.

5. The device of claim 1, further comprising a cam slot formed in the second movable handle, the slot including a pin locking cut-out and a pin travel portion; and a pin configured to move within the cam slot between the pin locking cut-out and the pin travel portion of the slot, the pin being configured to be seated in the locking cut-out when the first and second movable handles are moving together, and the pin being configured to slide in the pin travel portion of the slot during the second phase of travel.

6. The device of claim 5, further comprising a cam lever within the proximal handle portion, the cam lever having a second slot formed therein that includes a first leg and a second leg that extends transverse to the first leg; and
a second pin configured to move between the first leg and the second leg, the second pin being configured to slide in the first leg during the first phase of travel, and the second pin being configured to slide in the second leg during the second phase of travel.

7. The device of claim 6, wherein the cam lever is configured to push the pin through the elongate portion of the slot.

8. The device of claim 1, further comprising a pin seated in a first slot formed in the first movable handle and seated in a second slot formed in the second movable handle, the second slot being offset at an angle from the first slot, the proximal handle portion including a housing that has a third slot formed therein, the third slot being configured to force the pin into a first position in which the second movable handle is locked to the first movable handle during the first phase of travel, and to force the pin into a second position in which the second movable handle is unlocked from the first movable handle during the second phase of travel.

9. A surgical device, comprising:
a proximal handle portion including
a body portion having a first slot formed therein,
a first trigger configured to move relative to the body portion in a first actuation of the proximal handle portion,
a second trigger having a second slot formed therein that has an elongate portion and a cut-out region adjacent to and in communication with the elongate portion, the second trigger being configured to move relative to the body portion simultaneously with the first trigger in the first actuation, and the second trigger being configured to move relative to the first trigger and the body portion in a second actuation of the proximal handle portion, and
a first pin operatively coupled to and movable within the second slot, the first pin being configured to remain within the second slot during the first actuation, and the first pin being configured to slide in the elongate portion of the second slot during the second actuation;
an elongate shaft extending distally from the proximal handle portion;
an end effector coupled to a distal end of the elongate shaft, the end effector being configured to move from an open position to a closed position in response to the first actuation; and
a cutting element configured to translate through the end effector in response to the second actuation.

10. The device of claim 9, wherein, in response to the first actuation, the first pin is configured to automatically move to the elongate portion of the second slot from the cut-out region of the second slot.

11. The device of claim 9, further comprising a spring configured to move into contact with a surface of the second trigger in response to the first actuation so as begin applying a force to the second trigger.

12. The device of claim 11, wherein the spring is configured to slide along the surface of the second trigger during the second actuation.

13. The device of claim 11, wherein the force applied by the spring is configured to fix the second trigger in position with respect to the body portion and the first trigger until a manual force applied to the second trigger overcomes the force applied by the spring.

* * * * *